US006482851B1

(12) United States Patent
Danishefsky et al.

(10) Patent No.: US 6,482,851 B1
(45) Date of Patent: Nov. 19, 2002

(54) SYNTHESIS OF DYSIDIOLIDE AND USES THEREOF

(75) Inventors: Samuel J. Danishefsky, Englewood, NJ (US); Steven R. Magnuson, Hamden, CT (US); Neal Rosen, Englewood, NJ (US); Laura Sepp-Lorenzino, Lansdale, PA (US)

(73) Assignees: Sloan-Kettering Institute for Cancer Research, New York, NY (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/630,636

(22) Filed: Aug. 1, 2000

Related U.S. Application Data

(63) Continuation of application No. PCT/US99/02347, filed on Feb. 4, 1999.
(60) Provisional application No. 60/073,699, filed on Feb. 4, 1998.

(51) Int. Cl.[7] .............................................. A61K 31/34
(52) U.S. Cl. ...................... 514/473; 549/315; 549/430; 568/446
(58) Field of Search ................................ 549/315, 430; 514/473; 568/446

(56) References Cited

PUBLICATIONS

Baratte, B.; Meijer, L.; Galaktionov, K.; Beach, D. *Anticancer Res.* 1992, 12, 873. (Exhibit 1).
Gassman, P.G.; Chavan, S.P. *J. Org. Chem.* 1988, 53, 2392. (Exhibit 2).
Gassman, P.G.; Chavan, S.P. *Tetrahedron Lett.* 1988, 29, 3407. (Exhibit 3).
Gassman, P.G.; Chavan, S.P. *J. Chem. Soc., Chem. Commun.* 1989, 837. (Exhibit 4).
Gassman, P.G.; Singleton, D.A.; Wilwerding, J.J.; Chavan, S.P. *J. Am. Chem. Soc.* 1987, 109, 2182. (Exhibit 5).
Gunasekera, S.P.; McCarthy, P.J.; Kelly–Borges, M.; Lobkovsky, E.; Clardy, J. *J. Am. Chem. Soc.* 1996, 118, 8759. (Exhibit 6).
Hashimoto, Y.; Nagashima, T.; Hasegawa, M.; Saigo, K. *Chem. Lett.* 1992, 1353. (Exhibit 7).
Hashimoto, Y.; Saigo, K.; Machida, S.; Hasegawa, M. *Tetrahedron Lett.* 1990, 39, 5625. (Exhibit 8).
Millar, J.B.A.; Russell, P. *Cell* 1992, 68, 407. (Exhibit 9).
Sammakia, T.; Berliner, M.A. *J. Org. Chem.* 1994, 59, 6890. (Exhibit 10).
Sipf. P.; Xu, W. *Tetrahedron* 1995, 51, 4551 (Exhibit 11).
Yoon, T.; Danishefsky, S.J.; de gala, S. *Angew, Chem. Int. Ed. Engl.* 1994, 33, 85. (Exhibit 12).
PCT International Search Report of PCT/US99/02347 (Exhibit 13).

*Primary Examiner*—Amelia Owens
(74) *Attorney, Agent, or Firm*—John P. White; Cooper & Dunham LLP

(57) ABSTRACT

This invention provides a process for the preparation of a racemic mixture of dysidiolide a method for inhibiting growth of cancerous cells comprising contracting an amount of the racemic mixture of dysidiolide effective to inhibit the growth of said cells. Further provided is a method for treating cancer in a subject which comprises administering to the subject a therapeutically effective amount of the racemic mixture of dysidiolide.

17 Claims, 30 Drawing Sheets

Figure 2:
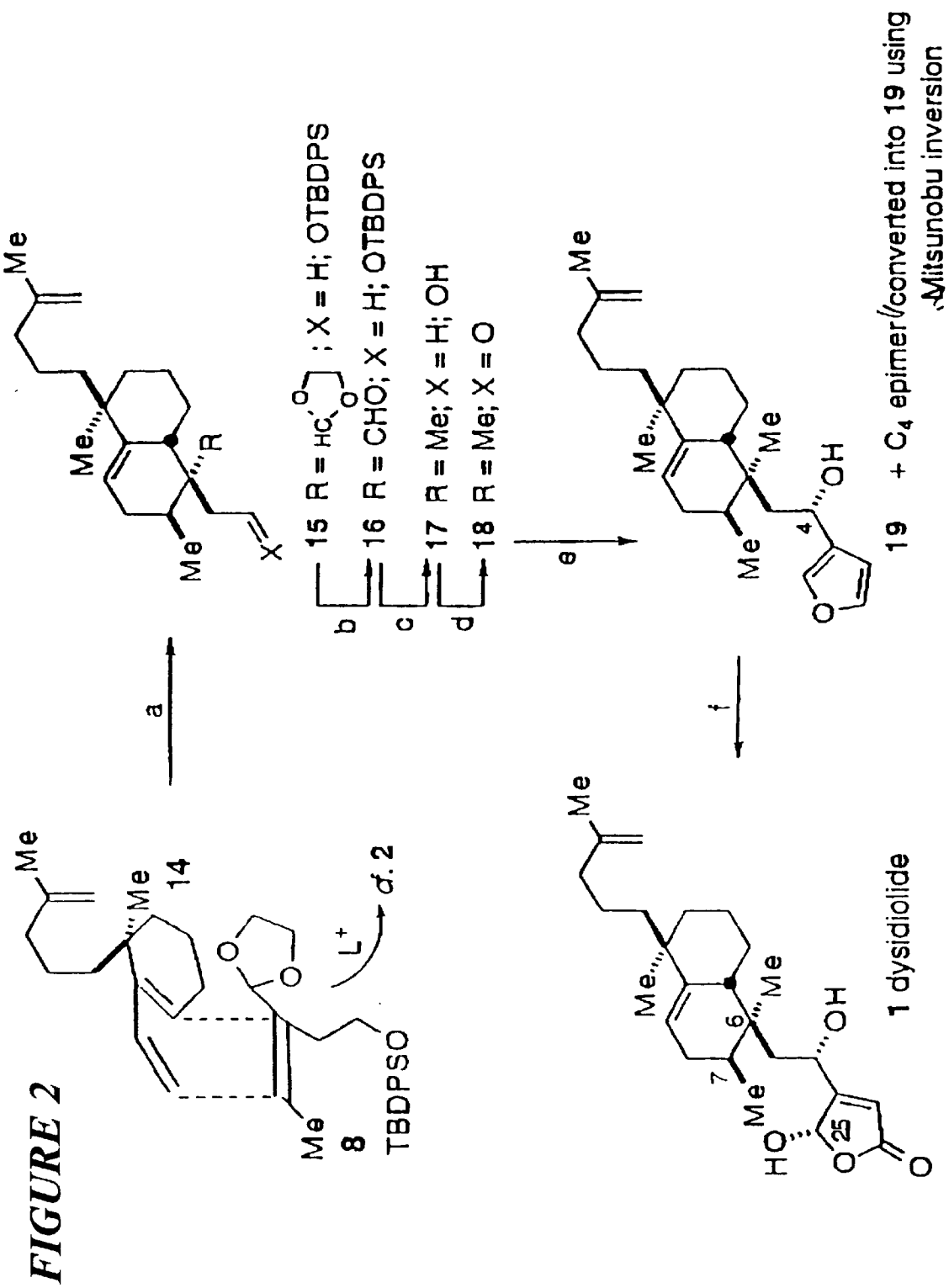
Figure 3A:
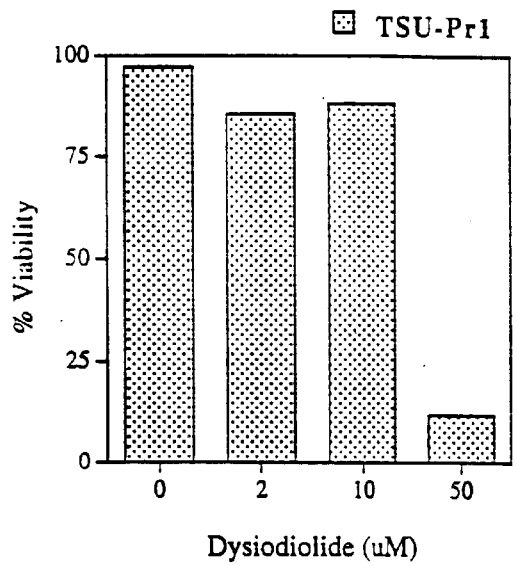
Figure 3B:
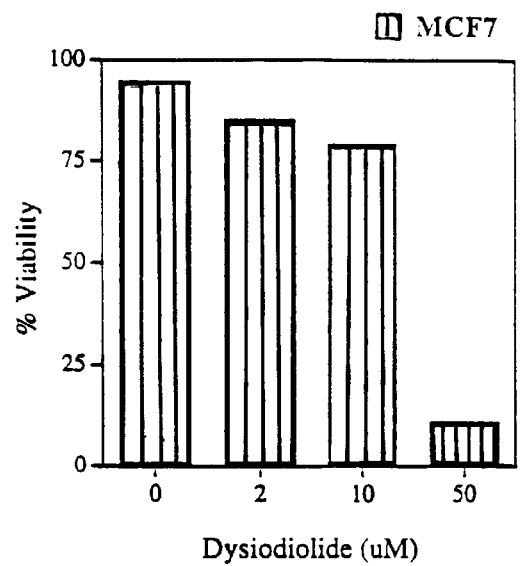
Figure 3C:
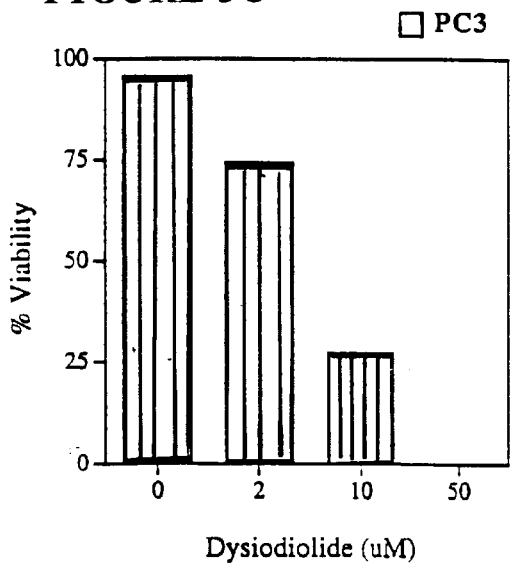
Figure 3D:
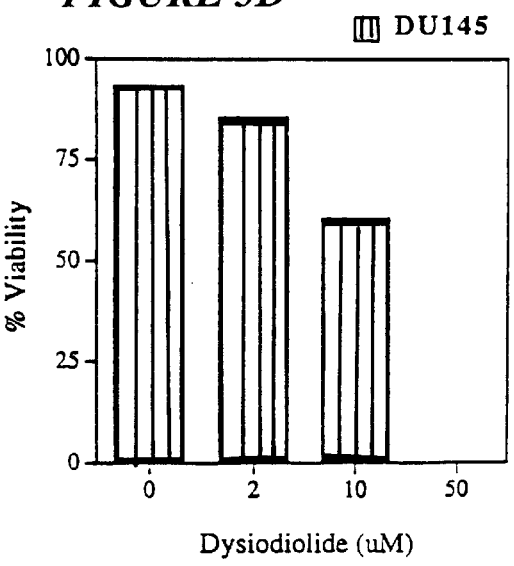
Figures 3, 4A:
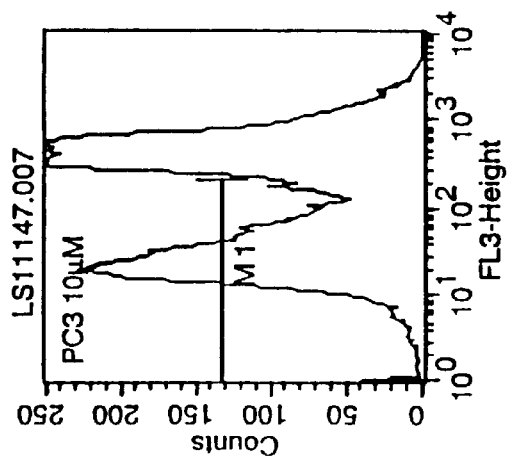
Figures 4, 4A:
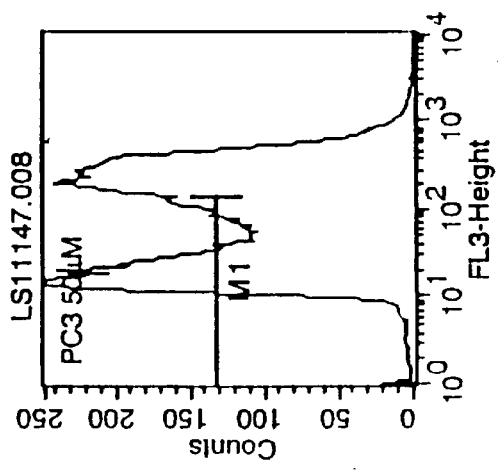
Figures 1, 2, 4B:
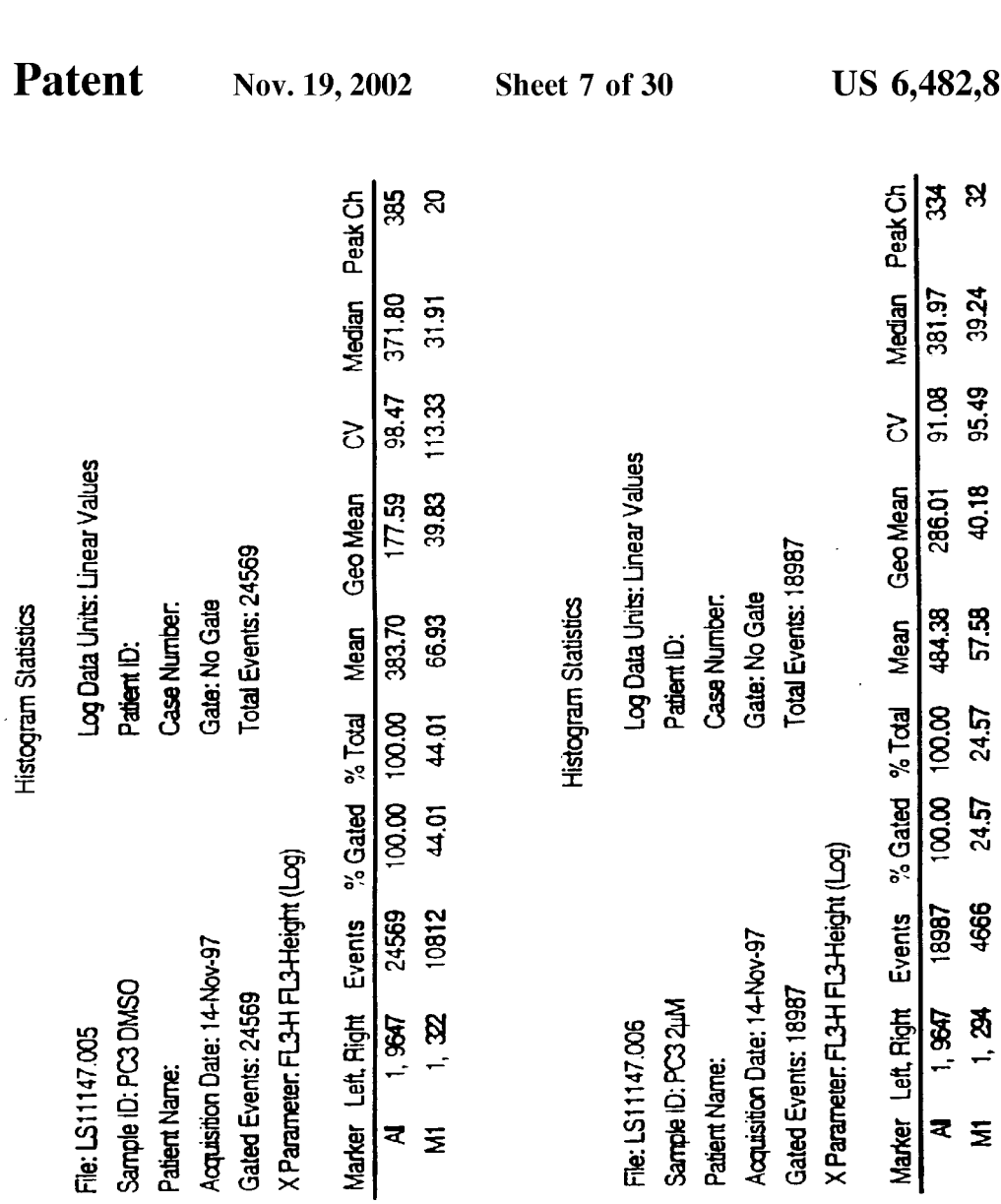
Figures 1, 4C:
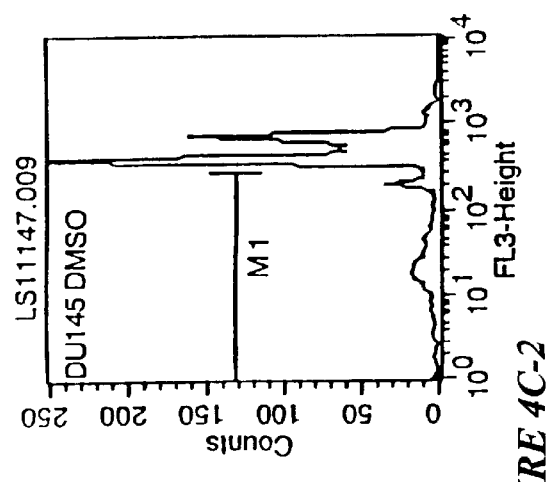
Figures 2, 4C:
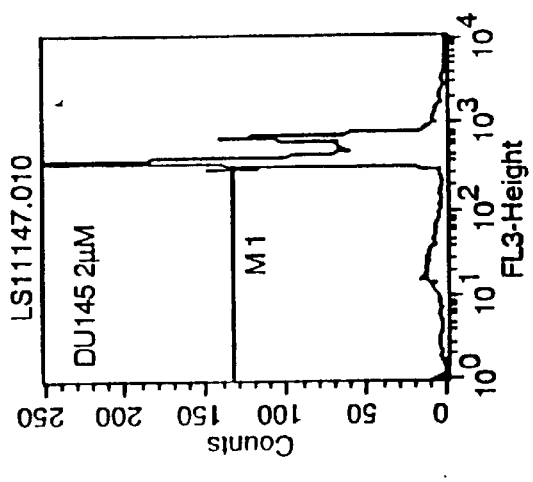
Figures 3, 4C:
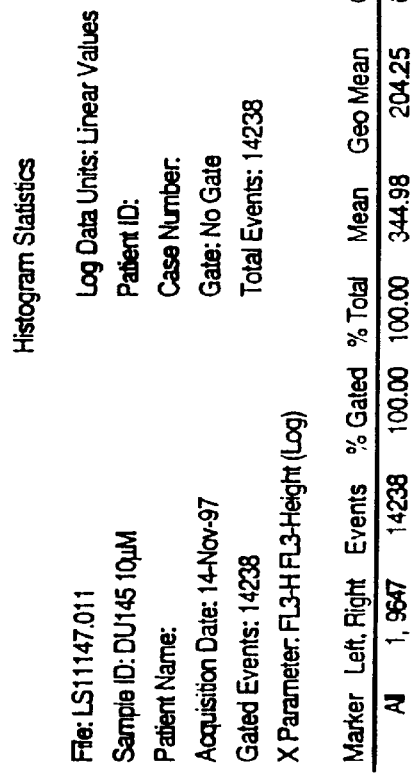
Figures 4, 4C:
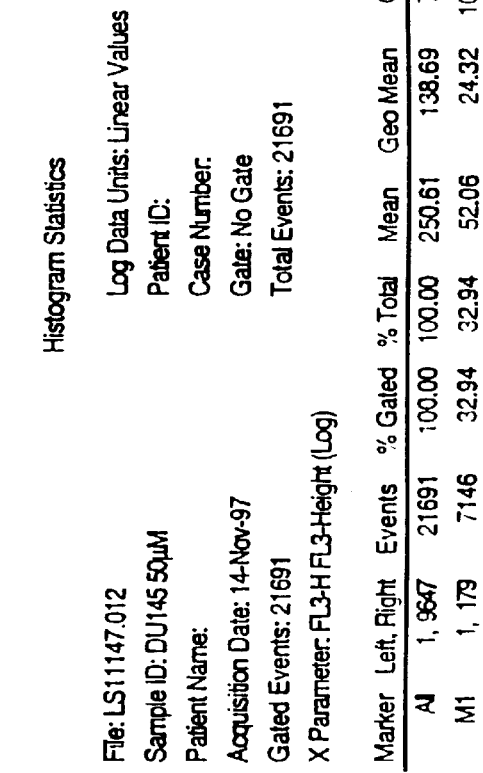

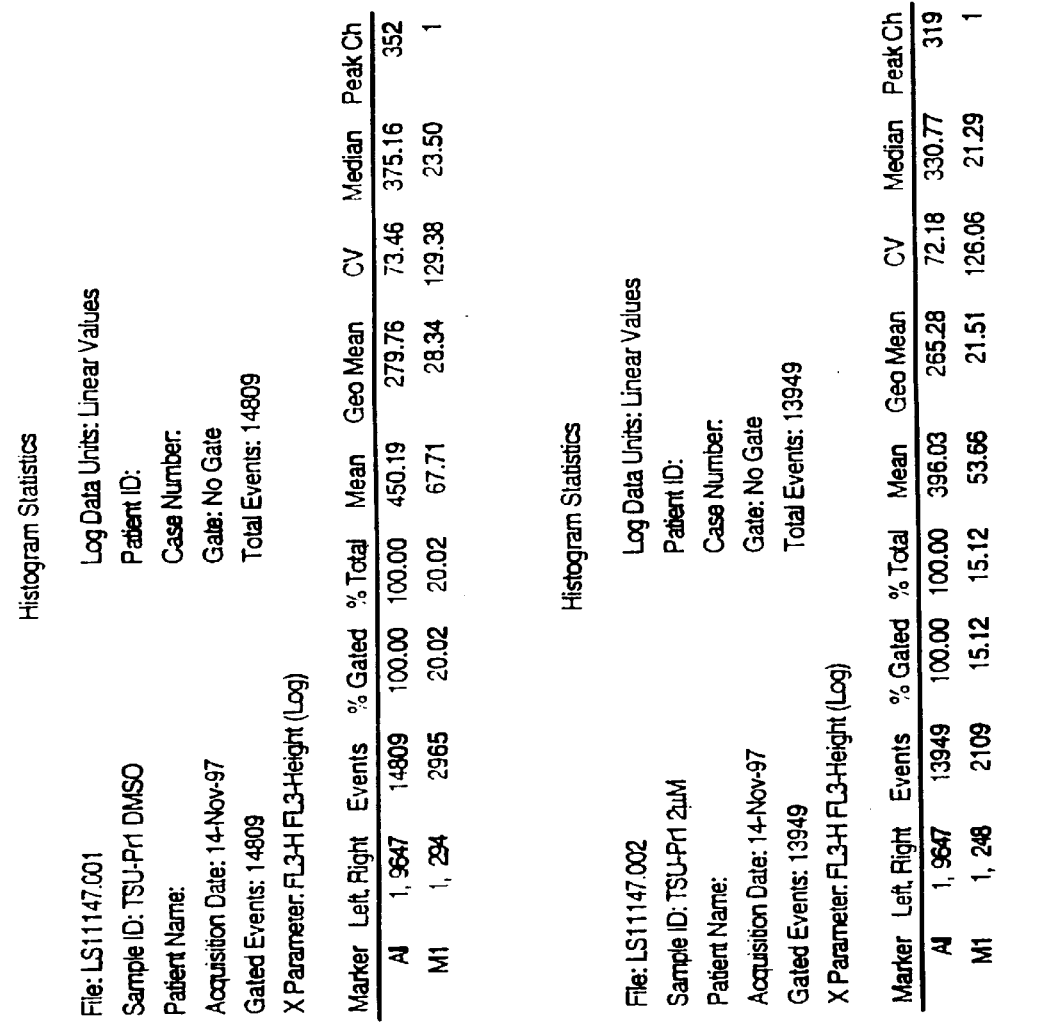
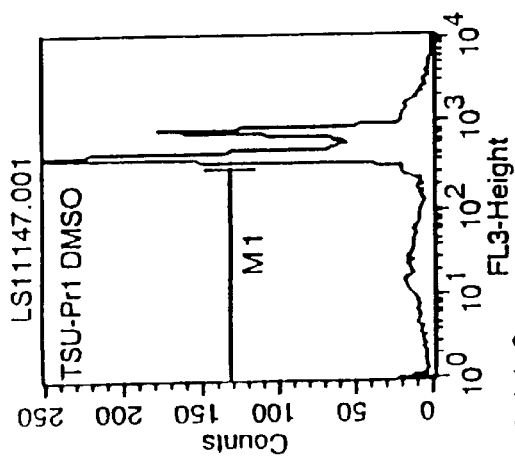
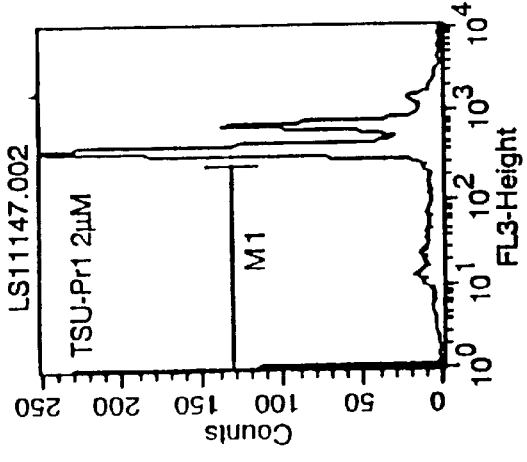
FIGURE 4A-1
FIGURE 4A-2

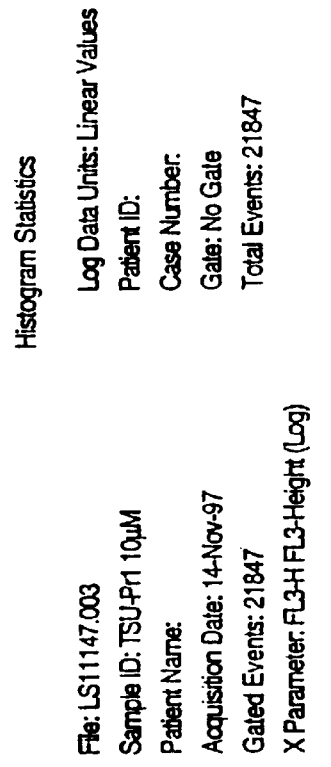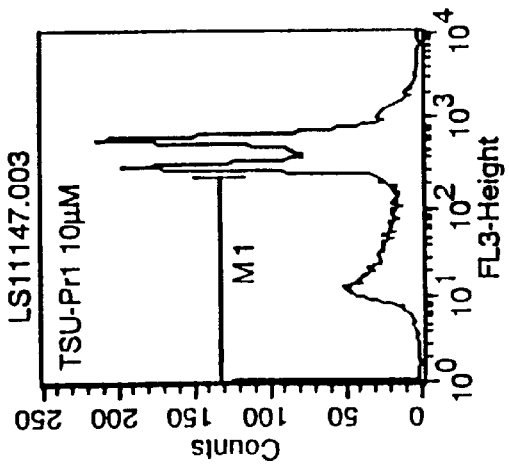
*FIGURE 4B-3*
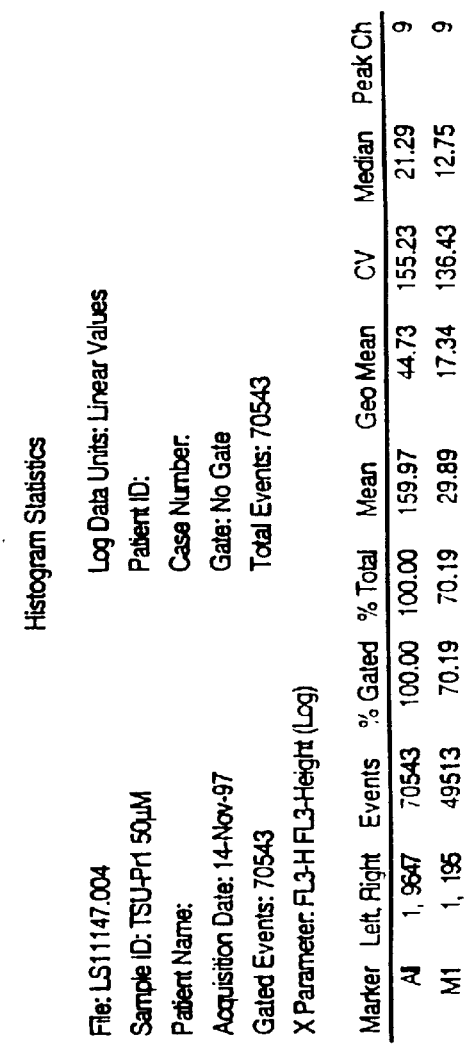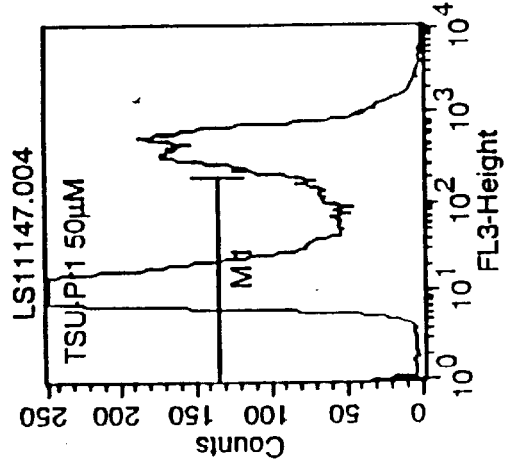
*FIGURE 4B-4*

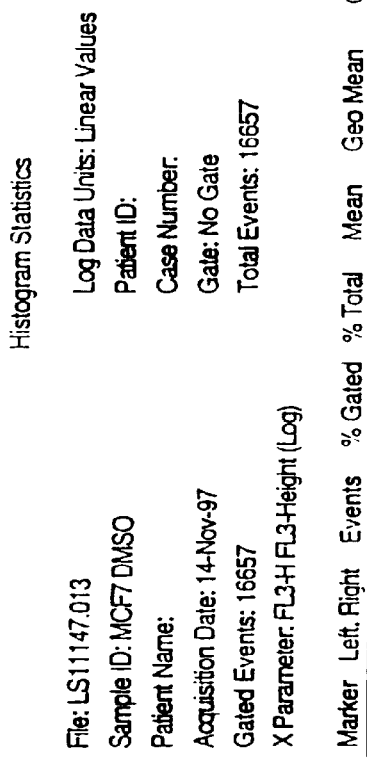
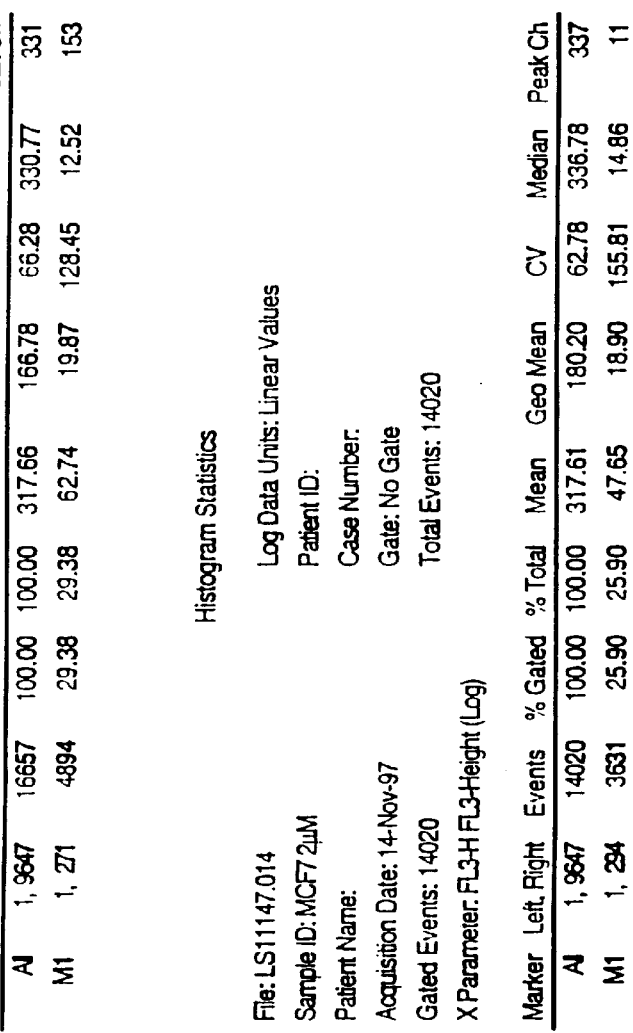
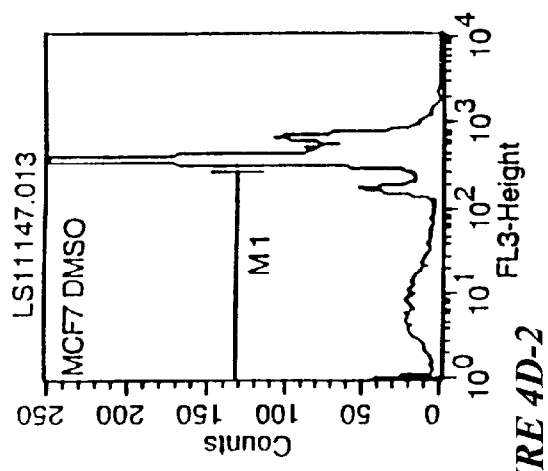
FIGURE 4D-1
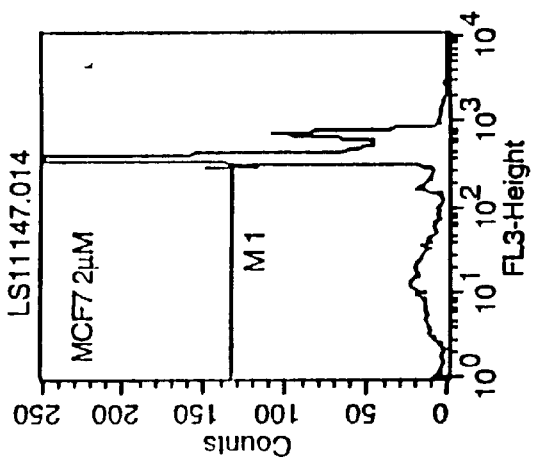
FIGURE 4D-2

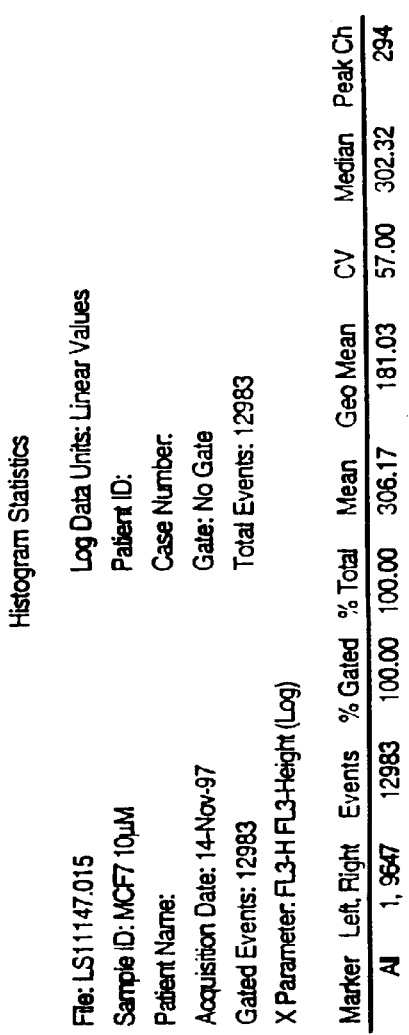
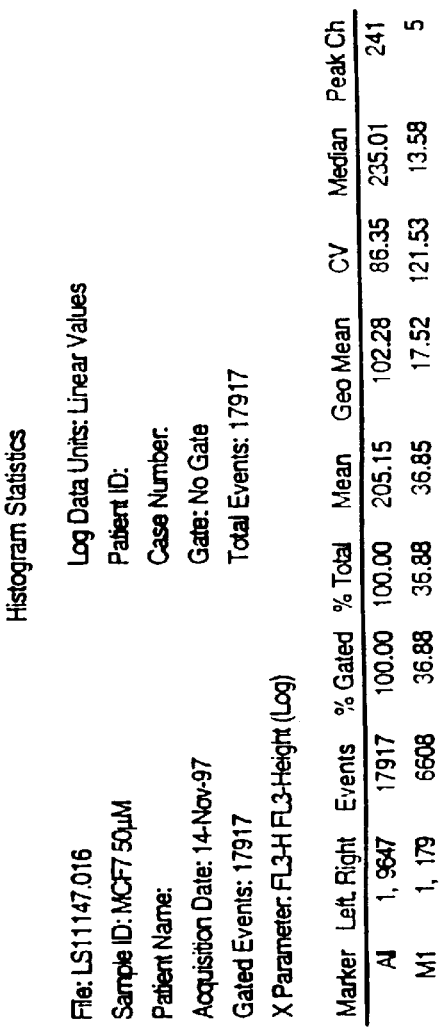
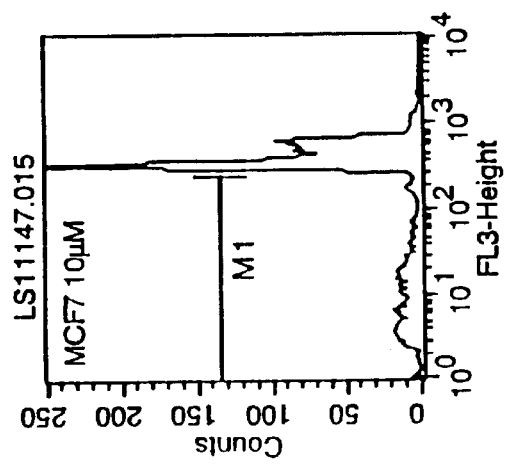
*FIGURE 4D-3*
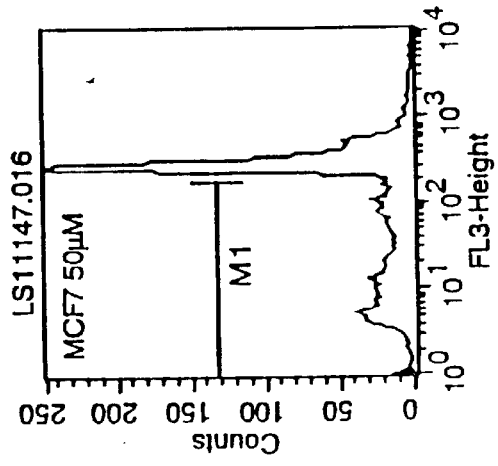
*FIGURE 4D-4*

*FIGURE 10B*

(G) (R)

| No. | Index | G | Area Name | PSL | Area (mm2) | PSL-BG | Ratio | % of Grp | PSL/mm2 | (P-B)/mm2 | Info |
|---|---|---|---|---|---|---|---|---|---|---|---|
| 1 | --- | - | - | 8425.00 | 63.36 | 8416.00 | --- | 60.90 | 133.00 | 132.80 | 100 |
| 2 | --- | - | + | 4844.00 | 63.36 | 4836.00 | --- | 35.02 | 76.46 | 76.32 | 57.5% |
| 3 | --- | - | - | 173.30 | 63.36 | 164.80 | --- | 1.25 | 2.73 | 2.60 | 100 |
| 4 | --- | - | + | 74.81 | 63.36 | 66.38 | --- | 0.54 | 1.18 | 1.05 | 40.3 |
| 5 | --- | - | - | 36.53 | 63.36 | 28.11 | 170.29 | 0.26 | 0.58 | 0.44 | --- |
| 6 | --- | - | - | 206.80 | 63.36 | 198.40 | 28.03 | 1.50 | 3.26 | 3.13 | 100 |
| 7 | --- | - | + | 64.56 | 63.36 | 56.14 | --- | 0.47 | 1.02 | 0.89 | 16.5 |
| 8 | --- | - | | 8.42 | 63.36 | --- | --- | 0.06 | 0.13 | --- | B |

2=Cdk2
1=Cdc2
4=Cdk4

FIGURE 12A
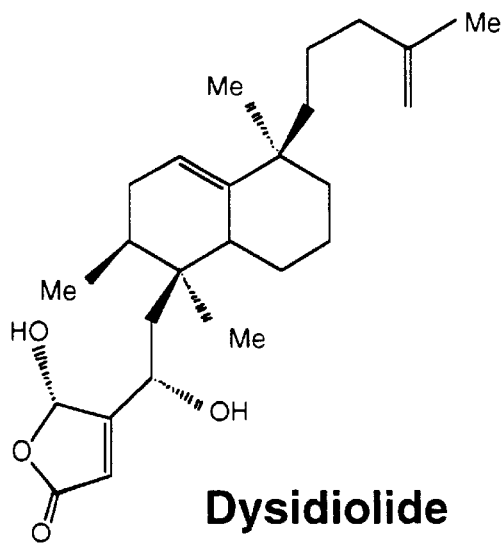
Dysidiolide
FIGURE 12B
| Human tumor cell lines | Origin | IC$_{50}$ (μM) |
|---|---|---|
| LNCaP | Prostate ca. | 1.72 |
| PC3 | Prostate ca. | 2.20 |
| 833K | Testicular ca. | 1.02 |
| SKOV3 | Ovarian ca. | 1.56 |
| SK MES1 | Lung sq. Ca. | 4.26 |
| CCRF-CEM | ALL | 0.57 |
| CCRF-CEM/VBL100 | VBL-R (527X) | 0.63 |
| MCF7 | Breast ca. | 1.09 |
| MCF7/Adr | Adr-R (4X) | 0.93 |
| HT29 | Colon ca. | 1.77 |
| A549 | Lung ca. | 1.47 |
FIGURE 12C
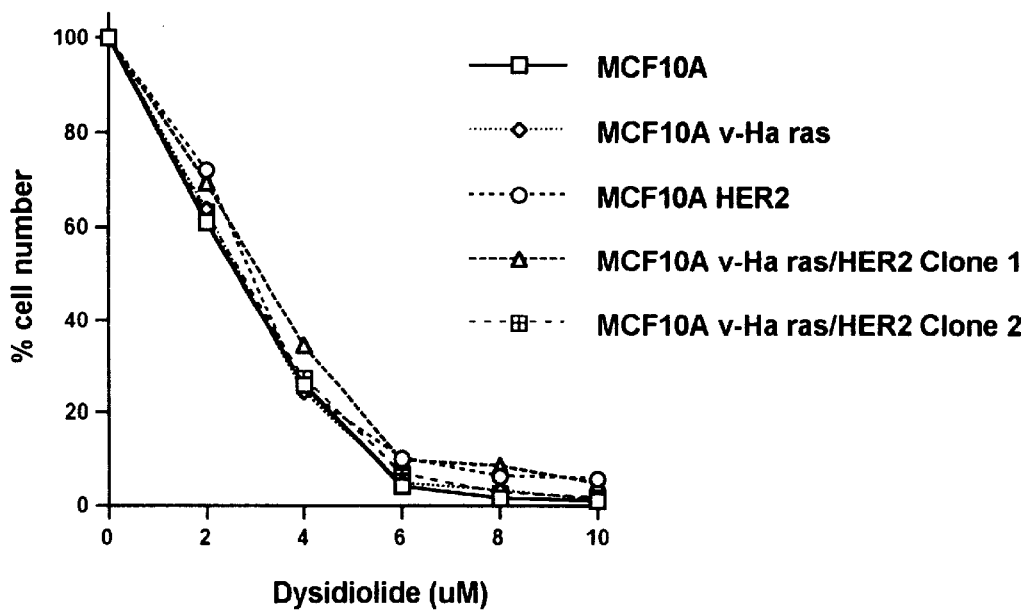

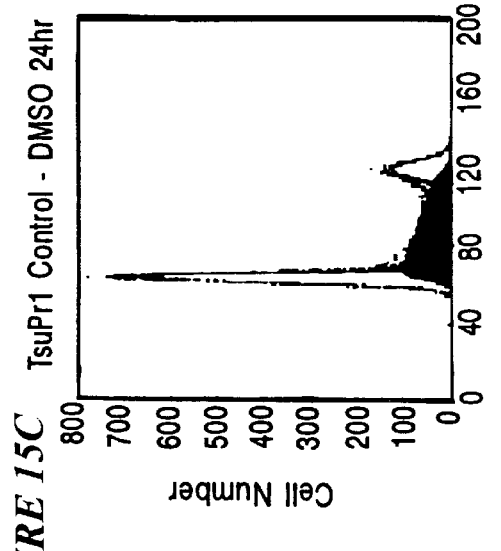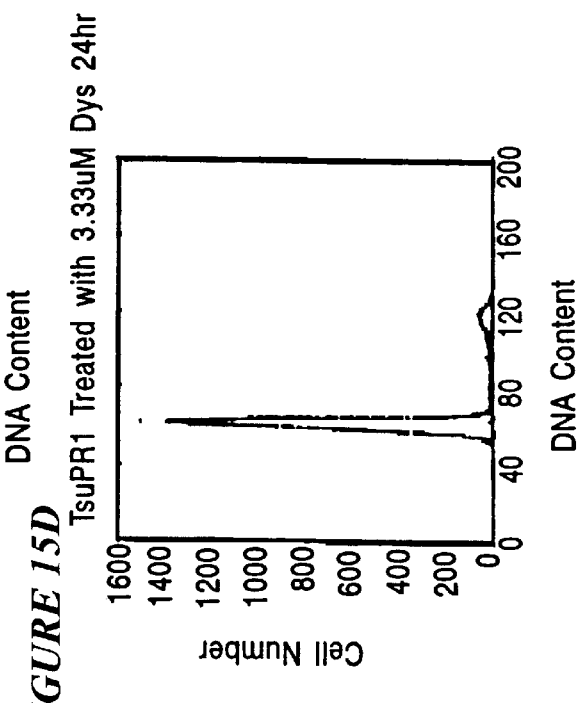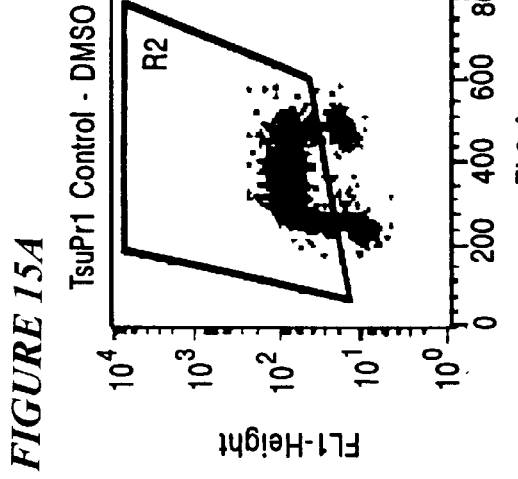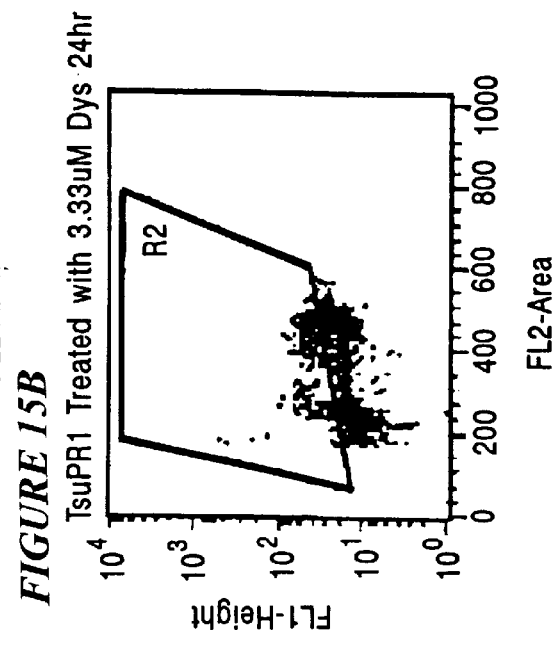
FIGURE 15C TsuPr1 Control - DMSO 24hr
FIGURE 15D TsuPR1 Treated with 3.33uM Dys 24hr
FIGURE 15A TsuPr1 Control - DMSO 24hr
FIGURE 15B TsuPR1 Treated with 3.33uM Dys 24hr

*FIGURE 17*

| Drug | Dose (mg/kg) | Average weight change (Gm) | | | | Average tumor volume (T/C) | | | N |
|---|---|---|---|---|---|---|---|---|---|
| | | Day 3 | Day 9 | Day 11 | Day 13 | Day 9 | Day 11 | Day 13 | |
| Control | 0 | 26.5 | -0.1 | 0.3 | 0.5 | 1 | 1 | 1 | 4 |
| Dysidiolide | 25 | 26 | 0.5 | -0.4 | 0.1 | 1.02 | 1.21 | 1.16 | 3 |
| | 63 | 27.8 | -1.8 | -4 | -5 | 0.71 | 0.48 | 0.31 | 2 |
| | 100 | 1/2 died of one injection | | | | | | | 2 |
| Taxol | 15 | 27.5 | -3 | -2.5 | -2.7 | 0.57 | 0.13 | 0.05 | 2 |

SYNTHESIS OF DYSIDIOLIDE AND USES THEREOF

This application is a continuation of PCT International Application No. PCT/US99/02347, filed Feb. 4, 1999, designating the United States of America, which is claiming the priority of U.S. Provisional Application No. 60/073,699, filed Feb. 4, 1998, the contents of which are hereby incorporated by reference into the present application.

The invention disclosed herein was made with Government support under NIH Grant Nos. HL25848(S.J.D.) and P50CA68425-02 from the Department of Health and Human services. Accordingly, the U.S. Government has certain rights in this invention.

Throughout this application, various references are referred to by Arabic numerals within parentheses. Disclosures of these publications in their entireties are hereby incorporated by reference into this application to more fully describe the state of the art to which this invention pertains.

BACKGROUND OF THE INVENTION

A variety of structurally fascinating and biologically active natural products can be obtained from marine sources. The isolation, structural formulation, and biological evaluation of natural products from the aquatic biomass constitutes a frontier of growing importance in chemistry. In some instances, where the structures are especially novel or the biological profiles of action hold particular promise, a program in total synthesis may be appropriate. Such a situation pertained in the case of the dysidiolide (1), a sesterterpene isolated from the marine sponge *Dysidea etheria* de Laubenfels. From a biogenetic point of view, dysidiolide corresponds to a novel cyclization mode of an acyclic $C_{25}$ isoprenoid precursor. Moreover, the difficulty available dysidiolide is a potent inhibitor of the human cdc25A protein phosphatase. (2,3) Since this enzyme complex (cdc25A, B and C) is involved in dephosphorylation at the $G_2/M$ transition of the cell cycle, it has been proposed that inhibitors could produce specific cell cycle arrest. Early results have shown that dysidiolide inhibits growth of lung carcinoma and murine leukemia cell lines. (1)

The total synthesis problem was approached from the perspective of testing a dioxolenium (Gassman) typed of activated dienophile. (4,5) A Diels Alder reaction of the type 2+4 was performed, wherein the presumed mechanistically active intermediate would undergo cycloaddition in the regio-sense indicated, and with tight diastereoface governance based on differing demands of $R_1$ and $R_2$. Most interesting was the matter of endo/exo selectivity. It would be necessary for the dioxolenium function to direct endo in the Diels Alder step. (4,5a,6) The realization of this line of thinking is described below in the context of a total synthesis.

SUMMARY OF THE INVENTION

The present invention provides a process for the preparation of dysidiolide of the formula:

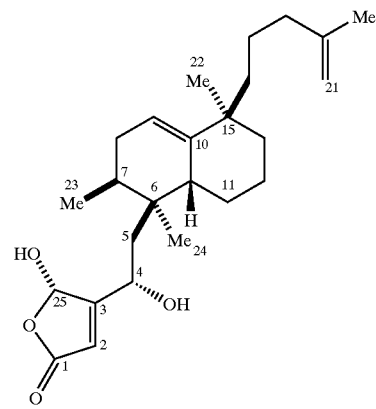

comprising the steps of:
(a) adding lithium dimethylcuprate to a dioxolane;
(b) trapping the compound formed in step (a) under suitable conditions to form an olefin;
(c) converting the ester function to a protected two carbon alcohol residue to form a dienophile;
(d) converting a ketone, derived by alkylating with an alkyl iodide, to a vinyl triflate;
(e) performing a Stille cross coupling on the vinyl triflate of (d) under suitable conditions to form a diene;
(f) performing a Diels Alder reaction on the dienophile of step (c) and the diene of step (e) under suitable conditions to form a compound having the structure:

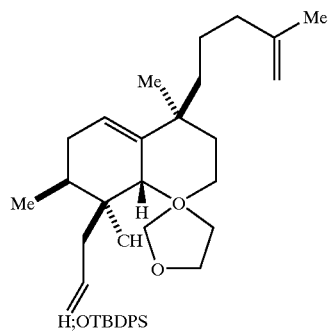

(g) cleaving the acetal function of the compound in (f) under suitable conditions to form a compound having the structure:

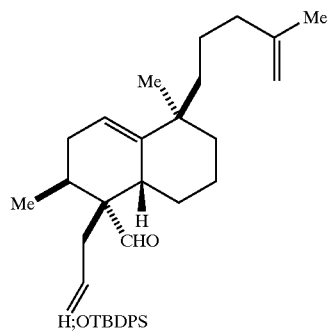

(h) performing a Wolff Kishner reduction and desilylating the compound in step (g) to form an alcohol having the structure:

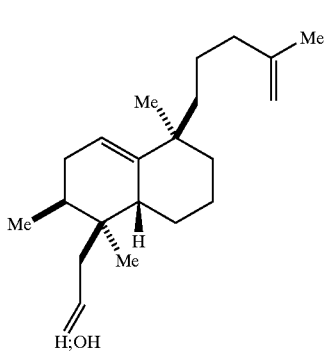

(i) oxidizing the alcohol formed in step (h) under suitable conditions to form an aldehyde;

(j) treating the aldehyde in step (i) with 3-lithiofuran and photo-oxidizing under suitable conditions to form a racemic mixture of dysidiolide.

The present invention further provides a product produced by the process.

Further, the present invention provides a pharmaceutical composition comprising a racemic mixture of dysidiolide.

Further, the invention provides a method for inhibiting growth of cancerous cells comprising contacting an amount of a racemic mixture of dysidiolide effective to inhibit the growth of said cells. Wherein the amount comprises a quantity of the compound to inhibit, reduce, or cause remission of the cells.

The present invention additionally provides a method for treating cancer in a subject which comprises administering to the subject a therapeutically effective amount of racemic mixture of dysidiolide. Where the cancer is of the breast, colon, lung, liver, brain or ovary and the therapeutically effective amount comprises an amount of the compound to inhibit, reduce, or cause remission of the cancer. Further, the therapeutically effective amount is an amount from about to 50 to about 5000 mm$^3$/day, 50 to about 500 mm$^3$/day, 60 to about 275 mm$^3$/day, 0.5 to 50 mg/kg body weight or about 5 to 10 mg/kg body weight. The administration comprises epidural, intraperitoneal, intramuscular, subcutaneous or intravenous injection; infusion; or topical, nasal, oral, anal, ocular or otic delivery.

This invention further provides a compound having the structure:

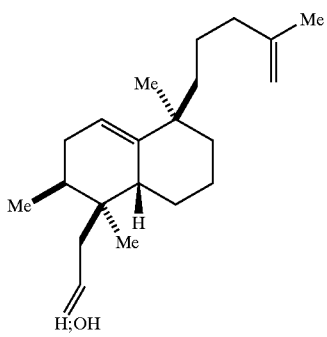

Additionally this invention provides a compound having the structure:

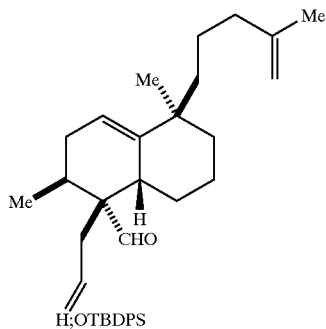

Finally, the present invention provides a compound having the structure:

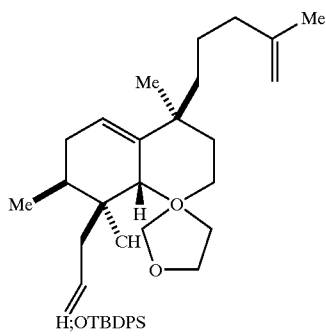

FIGURES

Figure 1A:
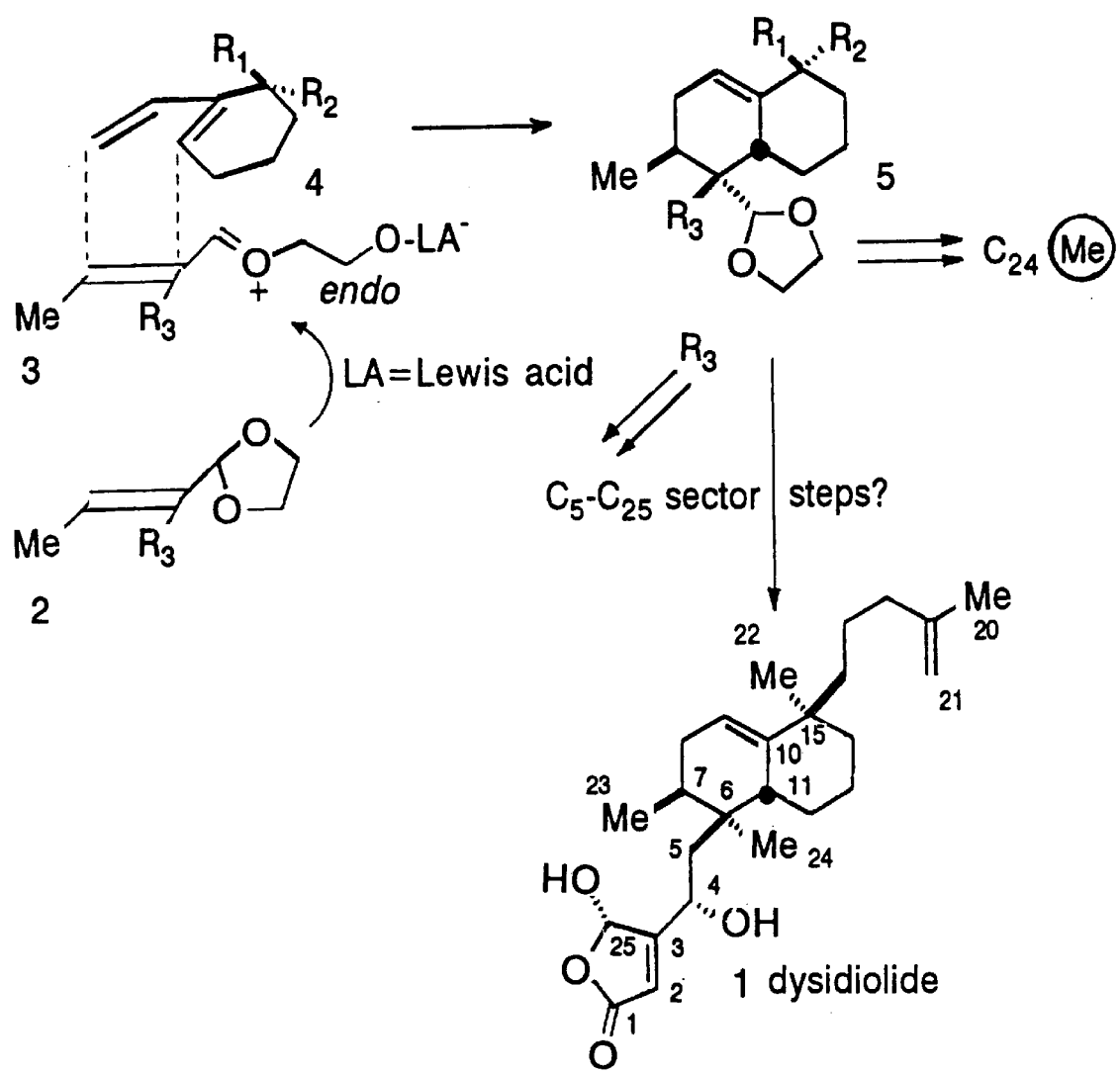
Figure 1B:
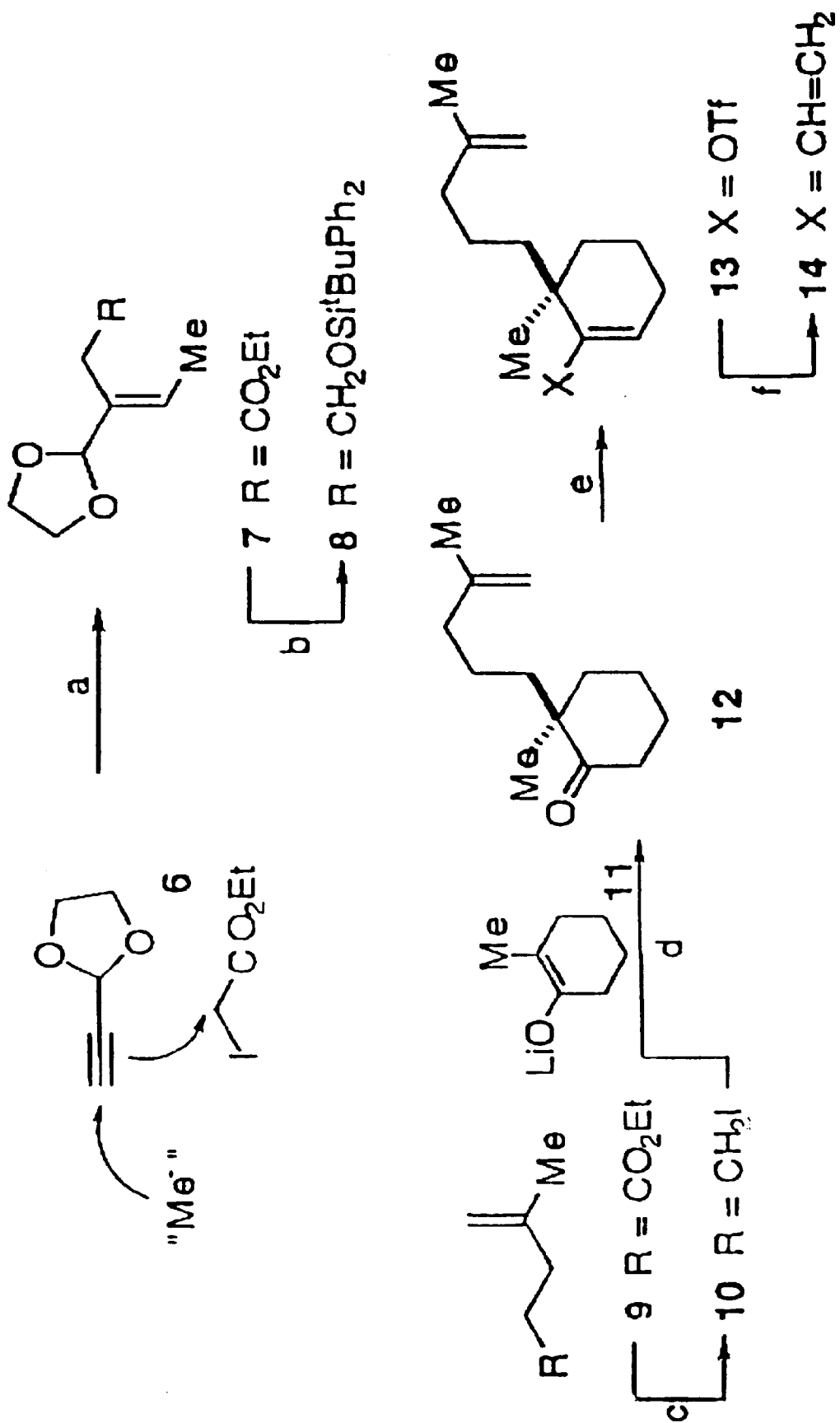

FIGS. 1A–B (A) Total synthesis of dysidiolide.

(B) Reagents and conditions: a) Me$_2$CuLi, Et$_2$O, −45° C.; ICH$_2$CO$_2$Et, HMPA, −55° C. to rt (30–55%). b) i. Superhydride, THF, −78° C. to −20° C.; imidazole, TBDPSCl, −20° C. to rt (68%). c) i. LAH, Et$_2$O; ii. TsCl, pyridine, 0° C.; iii. NaI, acetone, Δ (92% overall). d) DME, HMPA, −55° C. to rt (49%). e) Tf$_2$O, 2, 6-di butyl-4-methylpyridine, CH$_2$Cl$_2$ (87%). f) CH$_2$=CHSnBu$_3$, Pd(PPh$_3$)$_4$, LiCl, THF, Δ (80%).

FIG. 2

Reagents and conditions: a) TMSOTf, CH$_2$Cl$_2$,−90° C. (67%). b) montmorillonite K 10, CH$_2$Cl$_2$ (89%). c) H$_2$NNH$_2$, K$_2$CO$_3$, diethyleneglycol, 150° C. (74%). d) TPAP, NMO, ms CH$_2$Cl$_2$ (90%). e) 3-lithiofuran, THF, −78° C. (34%+56% C4 epimer). f) O$_2$, rose bengal, DIPEA, CH$_2$Cl$_2$, h, −78° C. (77%).

FIGS. 3A–D

Effect of dysidiolide on the viability of the human cancer cell lines (A) TSU-Pr1, (B) MCF7, (C) PC$_3$, and (D) DU145. Cultures were untreated or treated with 2, 10 or 50 μM dysidiolide for 24 hr. All cultures received a final DMSO concentration of 0.25%. Cells were harvested by trypsinization and viability was determined by Trypan blue exclusion.

FIGS. 4A–D

FACS analysis of (A) TSU-Pr1, (B) PC$_3$, (C) DU145, and (D) MCF7, untreated or treated with 2, 10 or 50 μM dysidiolide for 24 hr. All cultures received a final DMSO concentration of 0.25%.

Cells containing fragmented DNA content were detected as the M1 (subG1) region on DNA content plots.

FIGS. 5A–D

Cells with 2n to 4n DNA content were distributed on a DNA histogram and estimations for the percentages of cells in G1(2n), S(2n<X<4N) and G2/M (4n) were calculated using Becton-Dickinson FACS analysis software.

FIGS. 6A–D

Effect of 10 $\mu$M dysidiolide on cell cycle progression of S-phase MCF7 cells (BrdU-positive). MCF7 cultures were pulse-labeled with 10 $\mu$M BrdU for 30 min. Cultures were washed extensively with phosphate-buffered saline (PBS) solution and fresh media was added, supplemented or not with 10 $\mu$M dysidiolide. The final DMSO concentration of control and drug cultures was 0.05%. Cells were harvested at different times after the BrdU pulse and cells were stained for DNA content with propidium iodide, and for BrdU, with a monoclonal anti-BrdU antibody coupled to fluorescein. The progression of this group of cells through the cell cycle was followed by dual wavelength flow cytometry.

FIGS. 7A–F

Effect of 50 $\mu$M dysidiolide on cell cycle progression of S-phase MCF7 cells. MCF7 cells were pulse-labeled for 30 min with BrdU, and chased for 24 hr in the presence or absence of 50 $\mu$M dysidiolide. BrdU versus DNA content plots are shown for cell cultures harvested just after the pulse (time 0, "0"), and after the chase with ("24+") or without drug ("24–")

FIGS. 8A–B

DNA histograms of the subpopulation of MCF7 cells that stained positive for BrdU. Only the plots for (A) "0" and (B) "24–" are shown, as an example of a "forced fit".

FIGS. 9A–B

Effect of dysidiolide on the activity of Cdk2 and on the steady-state levels of Cdc25A and Cdc25C. MCF7 cells were treated for 2 or 4 hr with 0, 2 or 10 $\mu$M dysidiolide. A) The kinase activity of Cdk2 was assayed on immunoprecipitates using histone H1 as exogenous substrate. B) The steady-state levels of Cdc25 A and C were analyzed in total cell lysates with specific antibodies (Santa Cruz Biotechnology's sc097 and sc327 antibodies were used for detection of Cdc25 A and C, respectively).

Figure 10A:
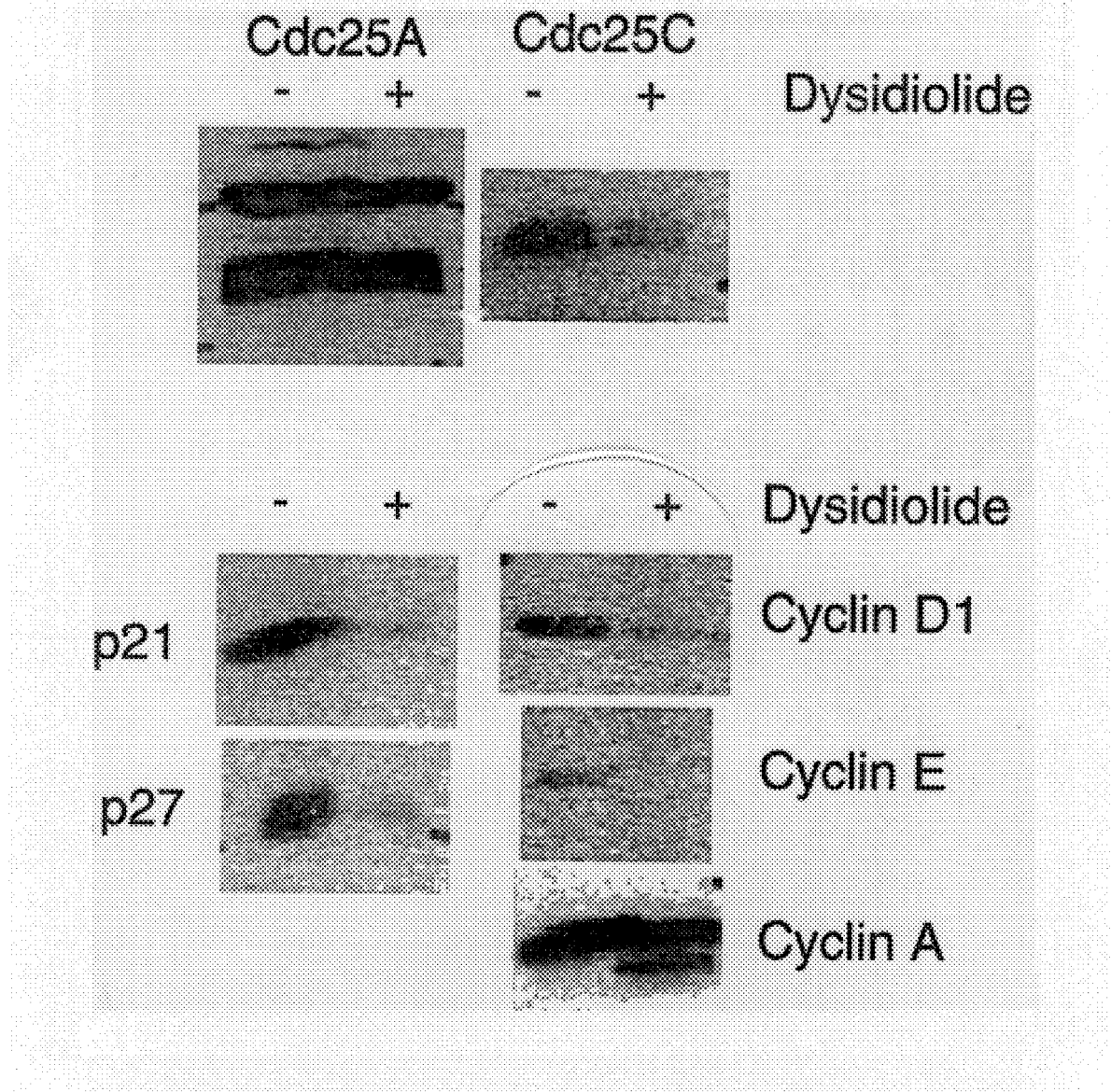
Figure 11:
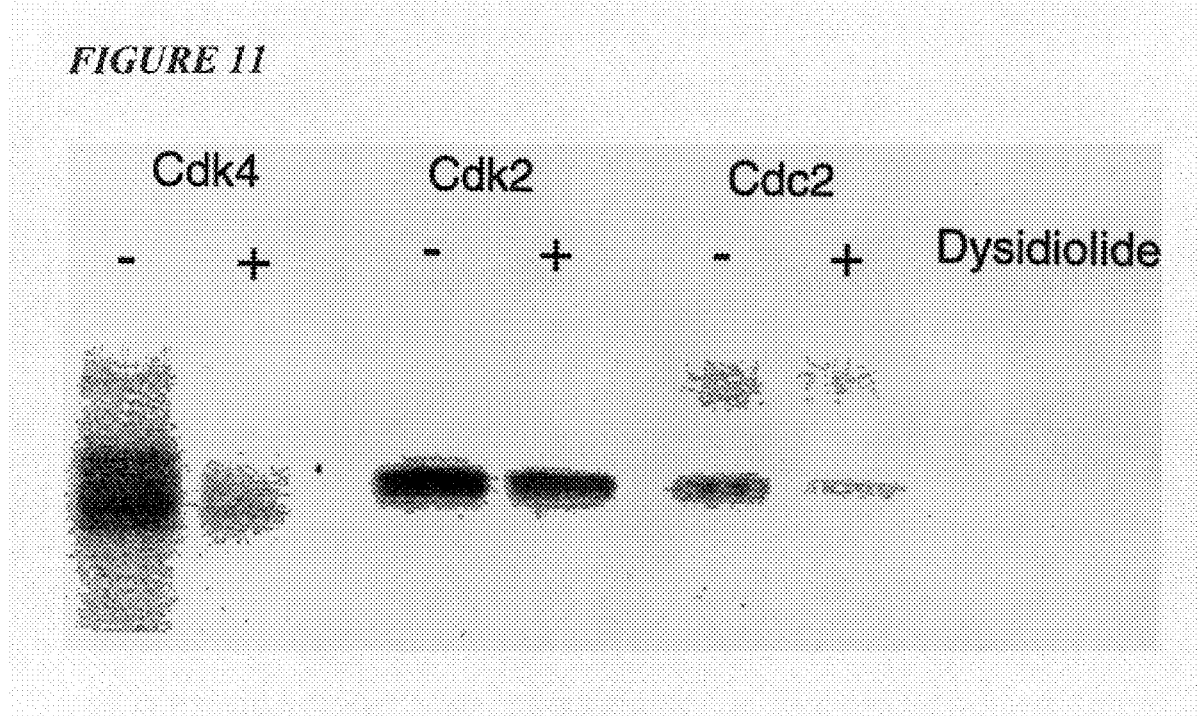
Figure 13B:
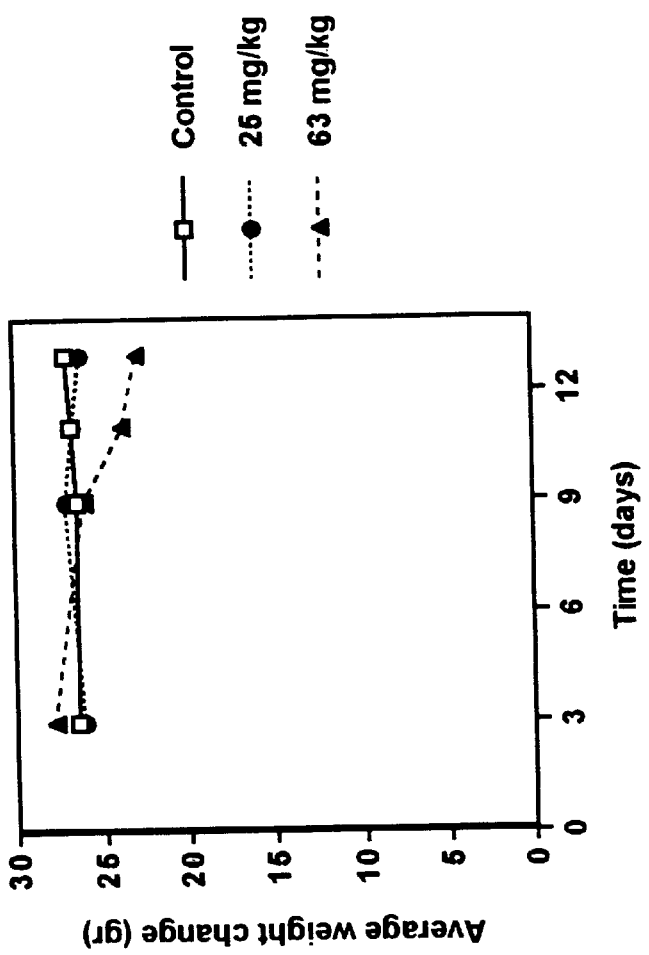
Figure 13A:
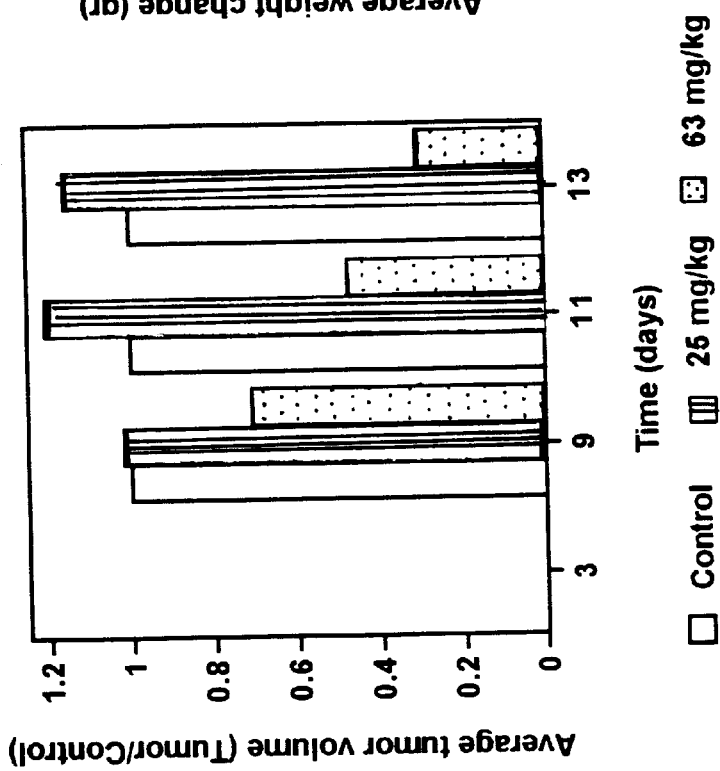
Figure 14A:
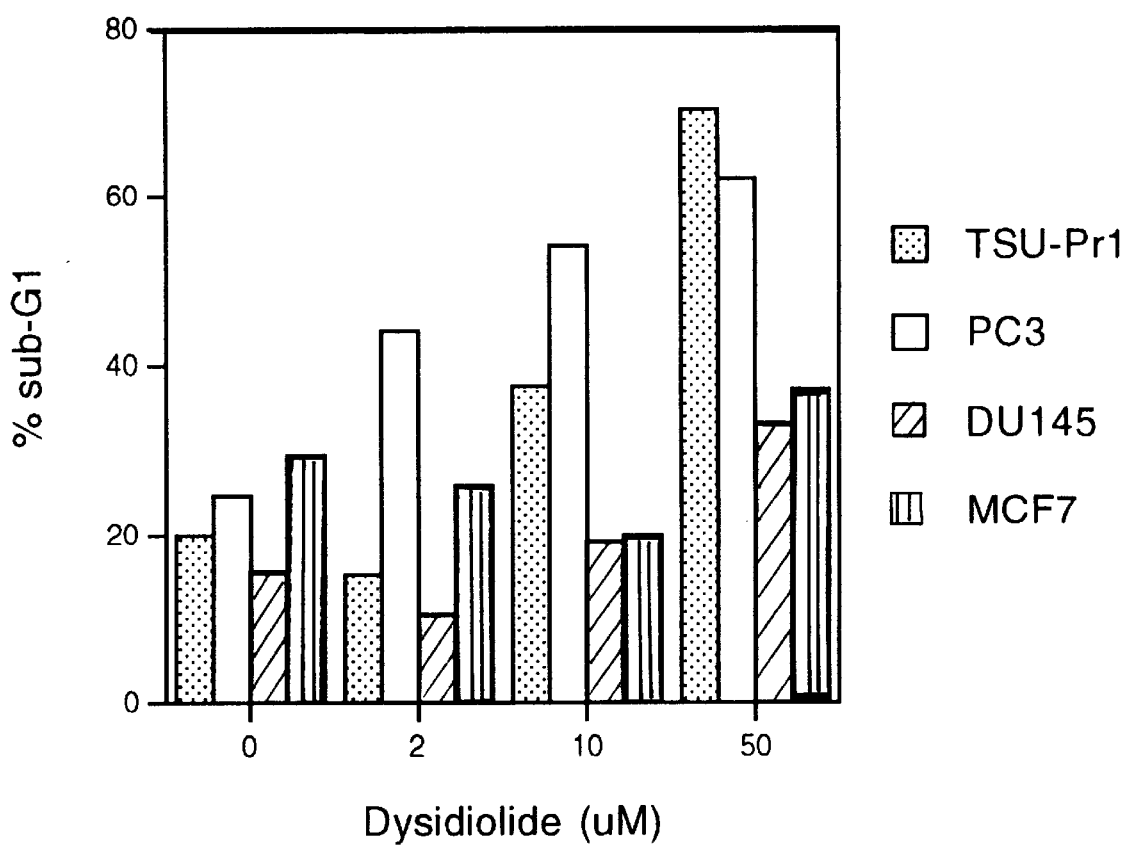
Figure 14B:
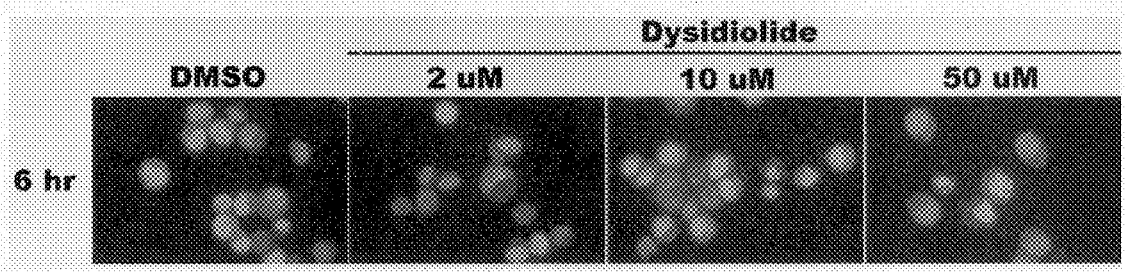
Figure 16:
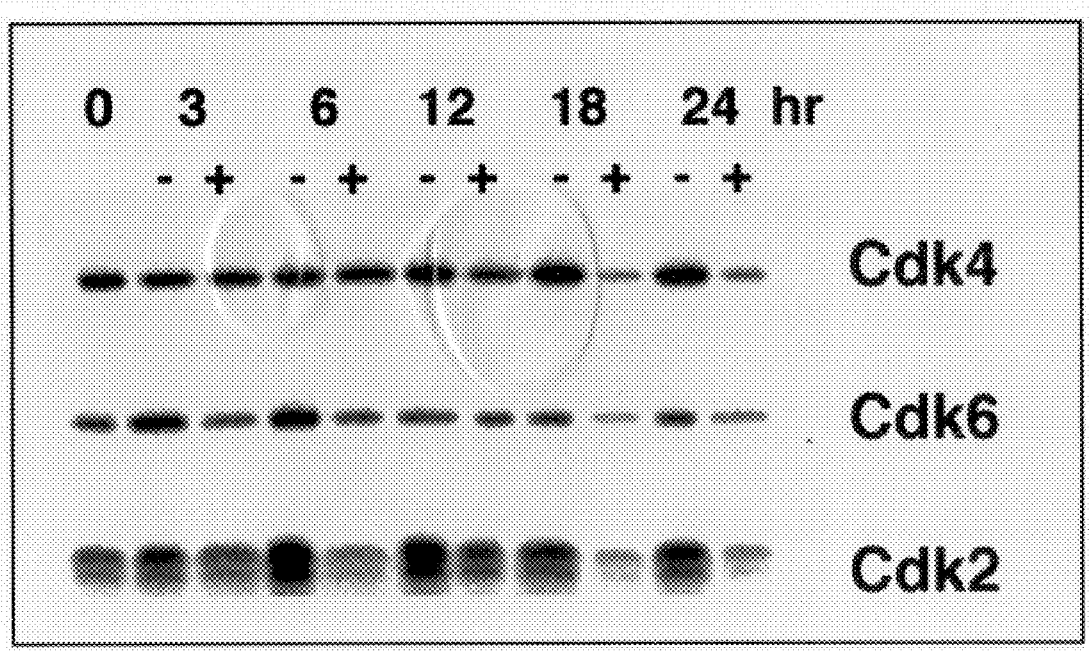

FIGS. 10A–B (A) Effect of 50 $\mu$M dysidiolide on the steady-state levels of Cdc25 A and C, and of other cell cycle regulators in MCF7 cells after a 24 hr treatment.

(B) Quantitation of the effect of dysidiolide on Cdk activity shown in 10A.

FIG. 11

Effect of a 24 hr treatment with 50 $\mu$M dysidiolide on the kinase activity of Cdk4, Cdk2 and Cdc2. Cdk were immunoprecipitated from MCF7 cell lysates obtained from cultures treated or not with dysidiolide for 24 hr. Histone H1 was used as substrate for Cdk2 and Cdc2, whereas GST-Rb was the substrate for Cdk4.

FIGS. 12A–C (A) Chemical structure of dysidiolide.

(B) Effect of dysidiolide on anchorage-dependent growth of human tumor cell lines. Cells were grown in multiwell plates and treated with either various drug concentrations or with dimethylsulfoxide (vehicle control). Cell number was determined and the inhibitory concentration to induce 50% growth inhibition (IC50) was determined. (C) Furthermore, dysidiolide inhibited the growth of immortalized human mammary epithelial cells transformed by either the oncogene ras, the receptor tyrosine kinase Neu, or both agents. Again, the IC50 for growth inhibition was in the low $\mu$M range (IC50 –3 $\mu$M dysidiolide).

FIGS. 13A–B

Dysidiolide inhibited the growth of MX1 tumor xenografts in nude mice. Sixty three mg/kg dysidiolide inhibited (A) tumor growth by 70% while (B) animal weight (and indication of overall toxicity) remained higher than 90% of controls.

FIGS. 14A–B

Effects of dysidiolide at the cellular level. Dysidiolide was cytotoxic to several human tumor cell lines. It induced apoptotic cell death in TSU-Pr1, PC3 and DU145 human prostrate cancer cells, as detected by the appearance of cells containing fragmented DNA via fluorescence-activated cell sorting (FACS). (A) Human tumor cells were treated for 24 hours in the presence of various concentrations of dysidiolide or DMSO vehicle. Cells were analyzed by FACS and the percentage of cells bearing less than the 2 n DNA complement was determined. (B) Immunofluorescence micrographs of TSU-Pr1 human prostrate cancer cells untreated or treated for 6 hours with 2–50 $\mu$M dysidiolide.

FIGS. 15A–D

Dysidiolide induces G1 arrest in TSU-Pr1 cells. TSU-Pr1 cells were treated for 24 hours with either DMSO or 3.33 $\mu$M dysidiolide. Cells were pulse-labeled for 30 min with bromodeoxyuridine (BrdU) and analyzed by FACS. The R@ window contains BRDU-positive, S-phase cells. Consistent with the proposed inhibitory effect of dysidiolide on the positive cell cycle regulator Cdc25. the drug inhibited the activity of cyclin-dependent kinases (Cdk). Cdk4, 6 and 2 were immunoprecipitated from DMSO- or drug-treated TSU-Pr1 cell cultures. Activity was examined in vitro kinase assays. The activity of the three Cdks was inhibited in drug-treated cells, as early as 3 hours in drug.

FIG. 16

In vitro kinase assays of Cdk. TSU-Pr1 cells were treated with 3.33 $\mu$M dysidiolide for 0–24 hours. Samples were collected at various times and the activity of Cdk4, 6 and 2 was determined. Cdks were immunoprecipitated with specific antibodies and incubated with radiolabeled ATP plus either histH1 (for Cdk2) or GST-Rb (for Cdk4 and 6). Reactions were separated on SDS-polyacrylamide gels and the amount of phosphorylated product was determined by radiometric analysis.

FIG. 17

Therapeutic Effects of Dysidiolide and Taxol in Nude Mice bearing MX-1. MX-1 cell 50 $\mu$g was implanted s.c. on day 0. Every other day i.v. treatments were given on day 3,5,7,9 and 11. The average tumor volume of control group on day 3, 7, 9, 11 and 13 were 62, 75, 113, 155 and 264 mm$^3$, respectively. Solvents: Dysidiolide [20–40 $\mu$l DMSO+100 $\mu$l (Cremophor: EtOH= 1:1)+Saline] Taxol [Clinical use (Cremophor+EtOH= 1:1)+Saline].

DETAILED DESCRIPTION OF THE INVENTION

The present invention provides a process claiming intermediate compounds. Each of the intermediate compounds is stable. Each intermediate compound having utility as a starting product for the synthesis of the racemic mixture of dysidiolide.

The present invention provides a process for the preparation of a racemic mixture of dysidiolide of the formula:

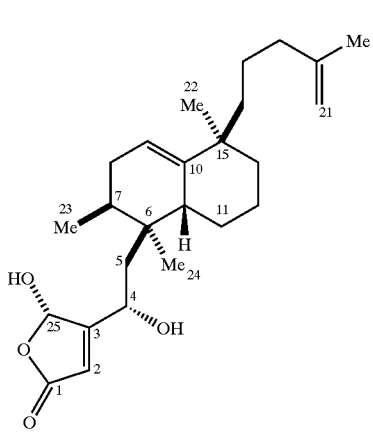

comprising the steps of:
(a) adding lithium dimethylcuprate to a dioxolane;
(b) trapping the compound formed in step (a) under suitable conditions to form an olefin;
(c) converting the ester function to a protected two carbon alcohol residue to form a dienophile;
(d) converting a ketone, derived by alkylating with an alkyl iodide, to vinyl triflate;
(e) performing a Stille cross coupling on the vinyl triflate of (d) under suitable conditions to form a diene;
(f) performing a Diels Alder reaction on the dienophile of step (c) and the diene of step (e) under suitable conditions to form a compound having the structure:

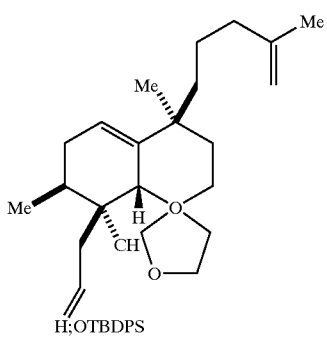

(g) cleaving the acetal function of the compound in (f) under suitable conditions to form a compound having the structure:

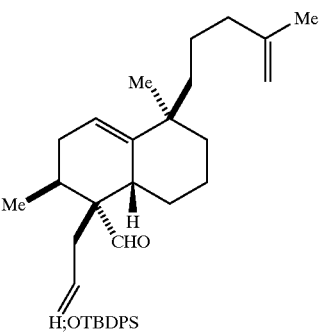

(h) Performing a Wolff Kishner reduction and desilylating the compound in step (g) to form an alcohol having the structure:

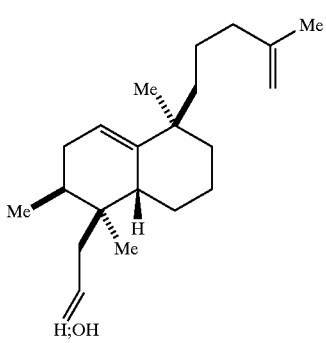

(i) oxidizing the alcohol formed in step (h) under suitable conditions to form an aldehyde;
(j) treating the aldehyde in step (i) with 3-lithiofuran and photo-oxidizing under suitable conditions to form a racemic mixture of dysidiolide.

The present invention further provides a product produced by the process.

This invention further provides a compound having the structure:

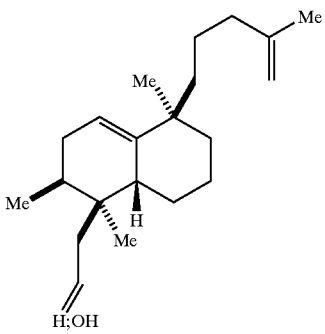

Additionally this invention provides a compound having the structure:

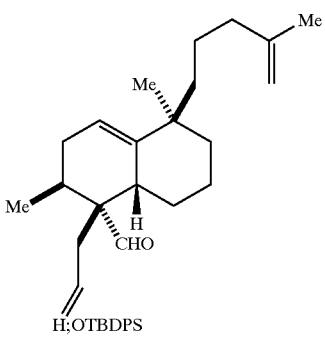

Finally, the present invention provides a compound having the structure:

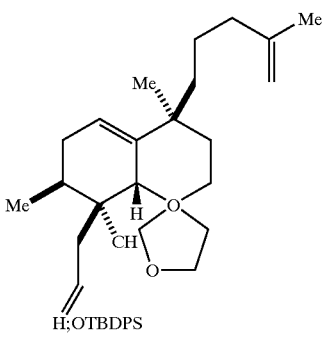

Further, the present invention provides a pharmaceutical composition comprising a racemic mixture of dysidiolide.

Further, the invention provides a method for inhibiting growth of cancerous cells comprising contacting an amount of a racemic mixture of dysidiolide effective to inhibit the growth of said cells. Wherein the amount comprises a quantity of the compound to inhibit, reduce, or cause remission of the cells.

The present invention additionally provides a method for treating cancer in a subject which comprises administering to the subject a therapeutically effective amount of racemic mixture of dysidiolide. Where the cancer is of the breast, colon, lung, liver, brain or ovary and the therapeutically effective amount comprises an amount of the compound to inhibit, reduce, or cause remission of the cancer. Further, the therapeutically effective amount is an amount from about to 50 to about 5000 mm$^3$/day, 50 to about 500 mm$^3$/day, 60 to about 275 mm$^3$/day, 0.5 to 50 mg/kg body weight or about 5 to 10 mg/kg body weight. The administration comprises epidural, intraperitoneal, intramuscular, subcutaneous or intravenous injection; infusion; or topical, nasal, oral, anal, ocular or otic delivery.

In the practice of any of the methods of the invention or preparation of any of the pharmaceutical compositions an "therapeutically effective amount" is an amount which is capable of inhibit, reduce, or cause remission of the cancer. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions capable of inhibiting neurotoxicity together with suitable diluents, preservatives, solubilizers, emulsifiers, adjuvants and/or carriers. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such. polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The carrier includes a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Synthesis of Dysidiolide

A highly concise total synthesis of the titled compound is described. The key step involves a Lewis Acid (TMSOTf) catalyzed Diels Alder reaction between vinyl cyclohexene and an $\alpha,\beta$-unsaturated dioxolane. The reaction manifests high regio- and diasterofacial selectivity. The dioxolane function (presumably reacting via its ring opened "onium" form) emerges endo. The dioxolane bearing carbon is eventually converted to a methyl group.

All air and moisture sensitive reactions were performed in a flame-dried apparatus under a nitrogen atmosphere unless otherwise noted. Air-sensitive liquids and solutions were transferred via syringe or cannula. Unless otherwise noted, all solvents and reagents were commercial grade and were used as sold.

High resolution mass spectra (HRMS) were determined by electron impact ionization (EI) on a JEOL JMS-DX 303HF mass spectrometer with perfluorokerosene (PFK) as an internal standard.

The specific version of compound 2 in FIG. 1 which was selected to serve as the operative dienophile was the acetal (compound 8 of FIG. 1B). The synthesis of this compound was accomplished starting with known dioxolane (compound 6 of FIG. 1B. (7) Addition of lithium dimethylcuprate to compound 6 of FIG. 1B followed by trapping with ethyl iodoacetate under the conditions indicated, (8) afforded olefin (compound 7 of FIG. 1B). The ester function was converted to a protected two carbon alcohol residue, to provide dienophile (compound 8 FIG. 1B).

The specific version of compound 4 of FIG. 1a selected as the operative diene was structure 14 of FIG. 1B. The synthesis of structure 14 of FIG. 1B commenced with the commercially available unsaturated ester (compound 9 of FIG. 1B). The latter was converted to known iodide (compound 10 of FIG. 1B) as described. (9) This compound served as an alklylating agent with respect to the lithium enolate of 2-methylcyclohexanone (compound 11 of FIG. 1B) (10) giving rise, albeit thus far in modest yield, to ketone (compound 12 of FIG. 1B). (9) This substance was converted to vinyl triflate (compound 13 of FIG. 1B) (12) and thence, by a Stille cross coupling, (13) to diene (compound 14 of FIG. 1B).

Diels Alder reaction between compound 8 of FIG. 1a and compound 14 of FIG. 1B was conducted under catalysis by TMSOTf (4b) as shown. There was thus obtained a 67% yield of adduct 15 of FIG. 2. (14) In addition, ca 5% of a stereoisomer (structure not yet determined) was obtained. From adduct 15 of FIG. 2, we advanced to dysidiolide in the manner shown. Cleavage of the ketal (15) in adduct 15 of FIG. 2 was followed by Wolff Kishner reduction of the aldehyde function in compound 16 of FIG. 2 to produce, upon concomitant desilylation, alcohol (compound 17 of FIG. 2). Following oxidation, aldehyde (compound 18 of FIG. 2) was in hand. Addition of 3-lithiofuran (16) to this compound, under the conditions shown, gave rise to (compound 19 of FIG. 2) and its $C_4$ stereoisomer. (17) Photooxidation of compound 19 of FIG. 2 with singlet oxygen,(16,18) provided a 77% yield of a racemic mixture of dysidiolide identical in all respects with the natural product by chromatographic and high field NMR criteria. (1) As is the case with the natural product, dysidiolide, in solution, exists as a mixture of $C_{25}$ diastereomers.

Upon crystallization, this carbon emerges in the relative configuration shown as compound 1 of FIG. 1a. (1)

In vivo and in Vitro Testing

Investigation of the biological profile of the synthesized dysidiolide racemic mixture resulted in growth arrest on four human cancer cell lines within 24 hours, dysidiolide (2–50 $\mu$M). In PC3, TSU-Pr1 and DU145 prostate cancer cells, growth arrest was accompanied by massive apoptosis. In the MCF7 breast cancer cell line, the drug caused loss of the $G_2/M$ peak and accumulation of cells in $G_1$. These data are consistent with the induction by dysidiolide of cell cycle specific growth arrest followed by apoptosis—a form of programmed cell death-in human cancer cells.

Figures 1, 5A:
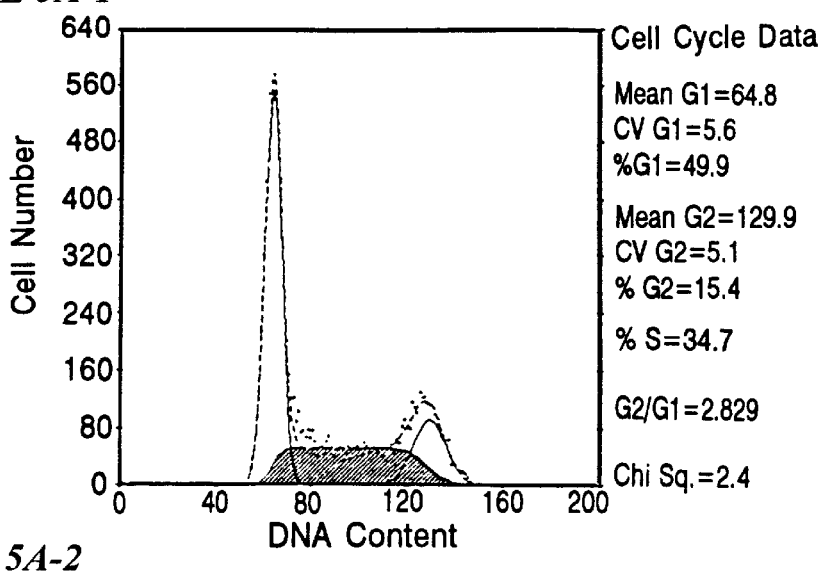
Figures 2, 5A:
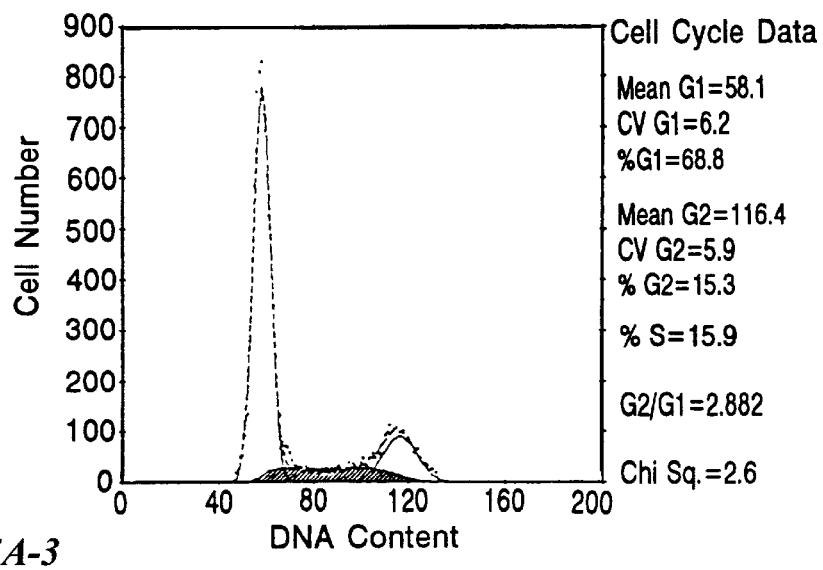
Figures 3, 5A:
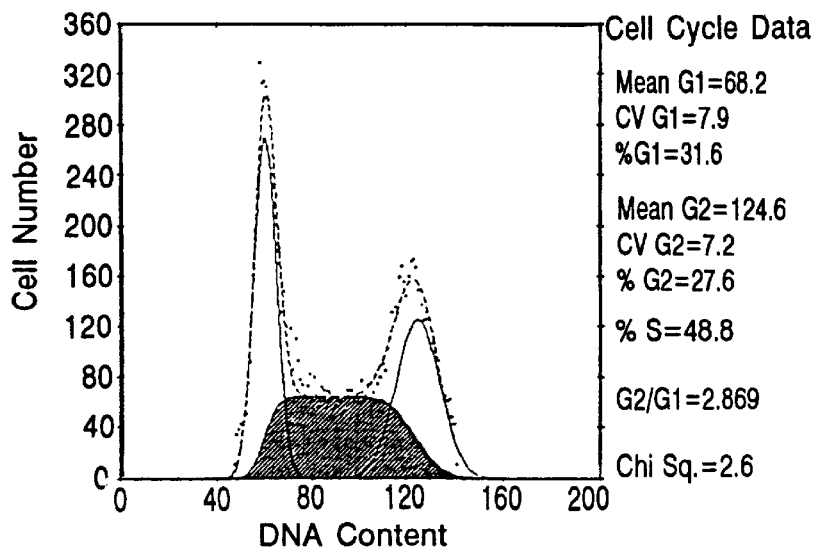
Figures 1, 5B:
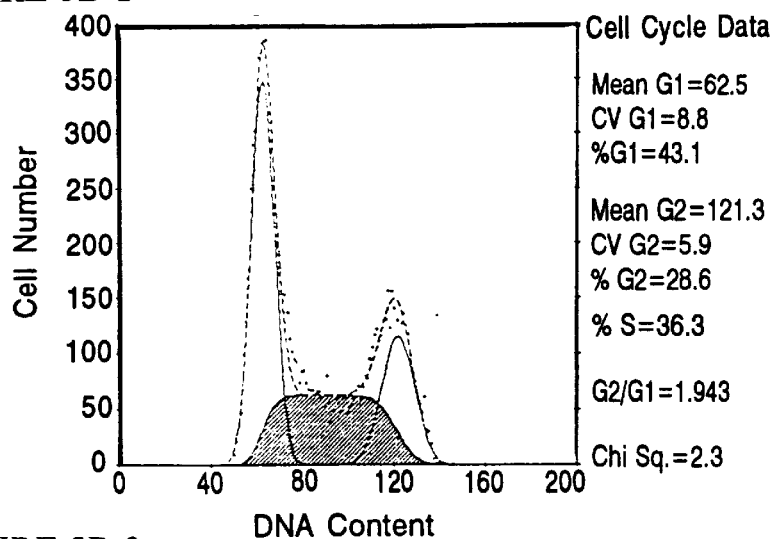
Figures 2, 5B:
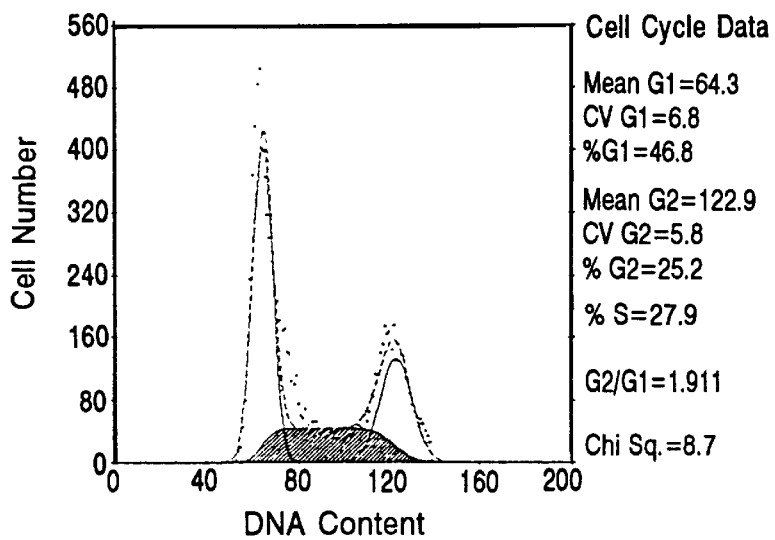
Figures 3, 5B:
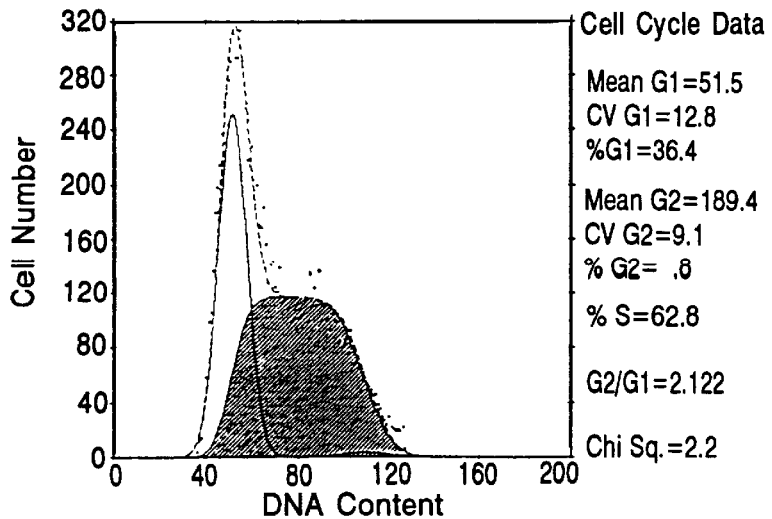
Figures 3, 5C:
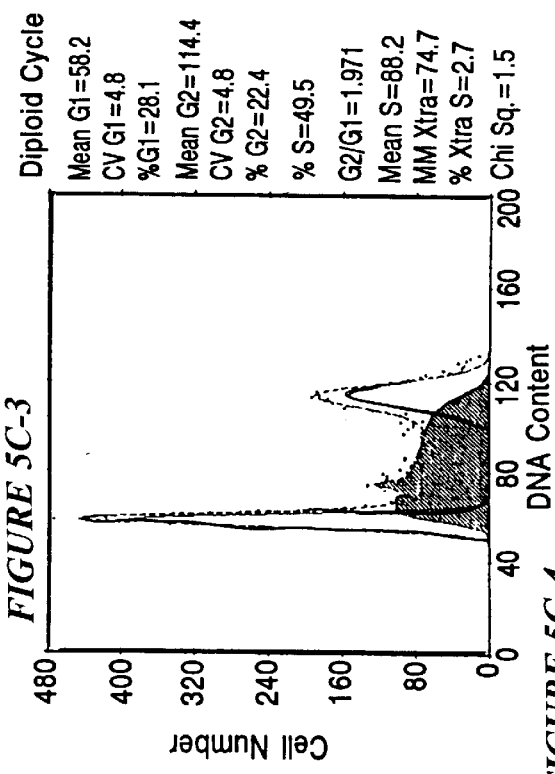
Figures 4, 5C:
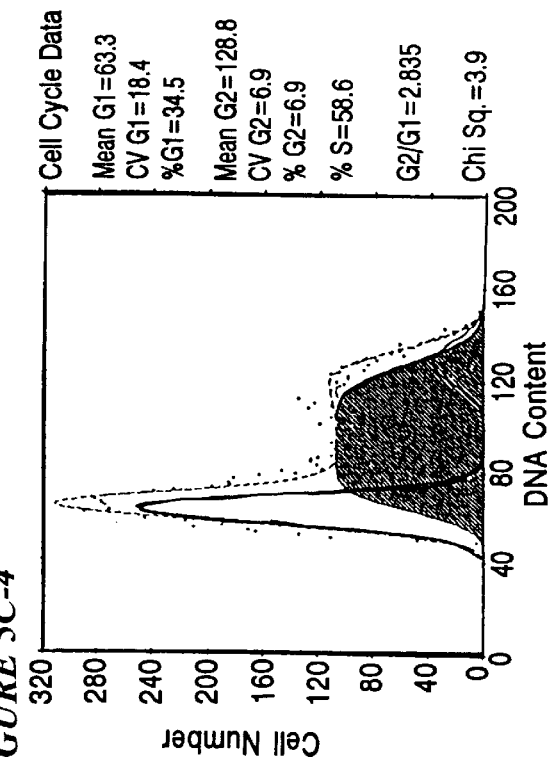
Figures 1, 5C:
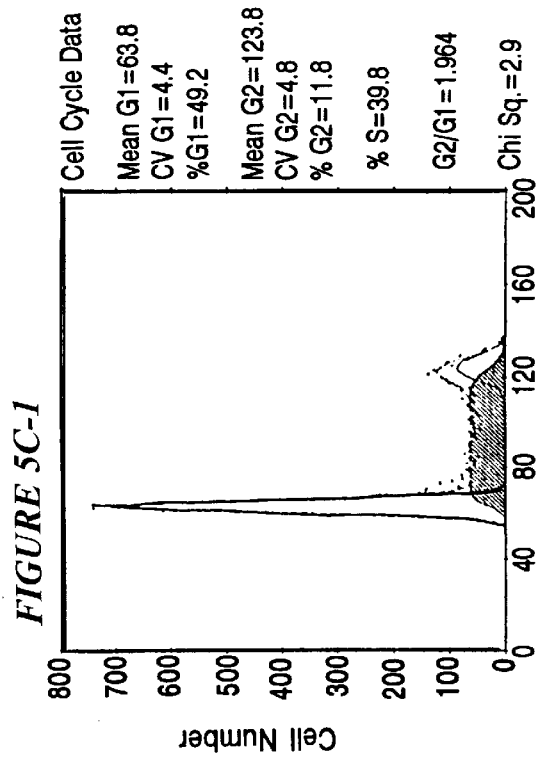
Figures 2, 5C:
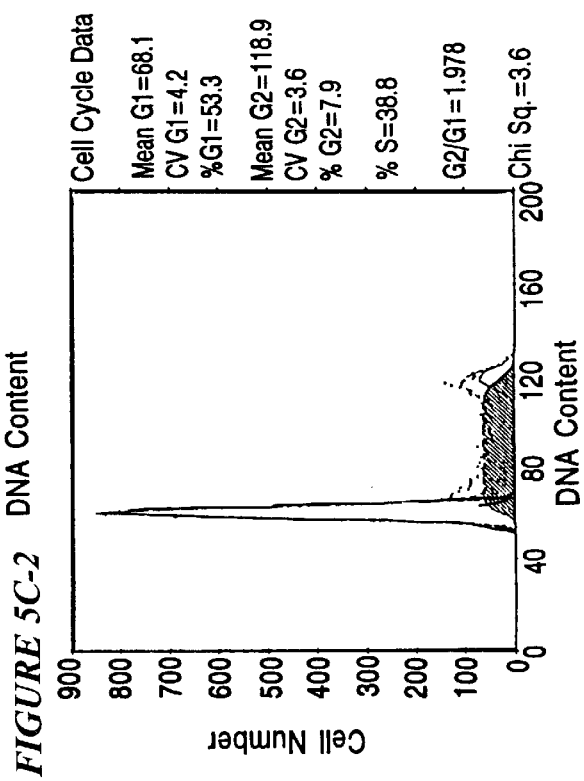
Figures 1, 5D:
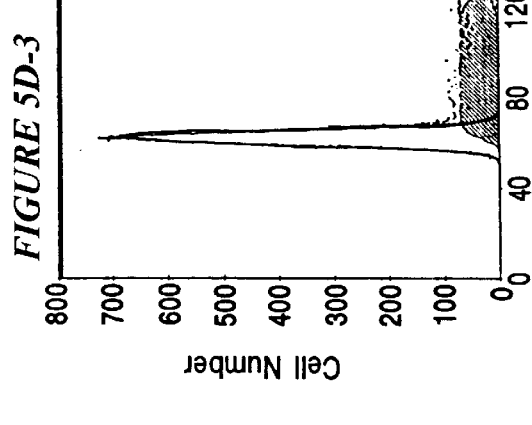
Figures 2, 5D:
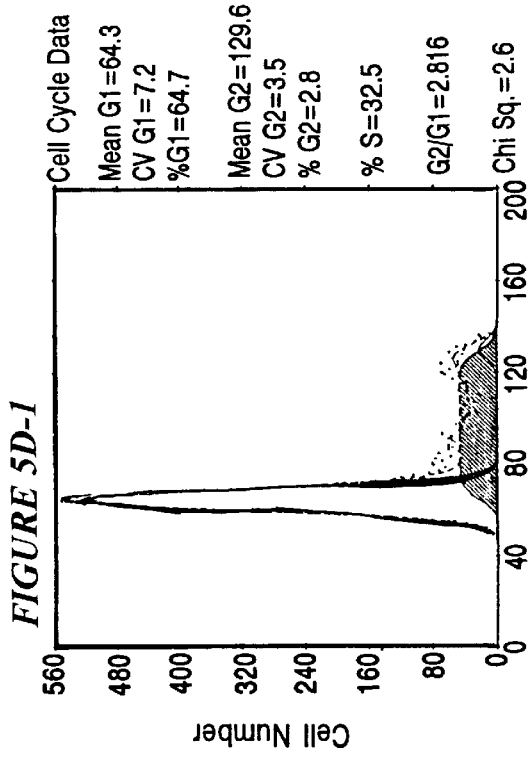
Figures 3, 5D:
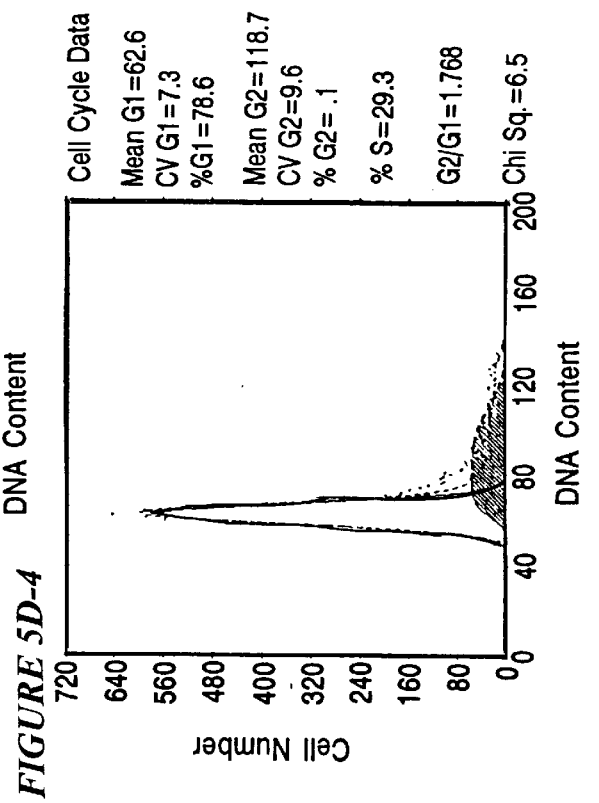
Figures 4, 5D:
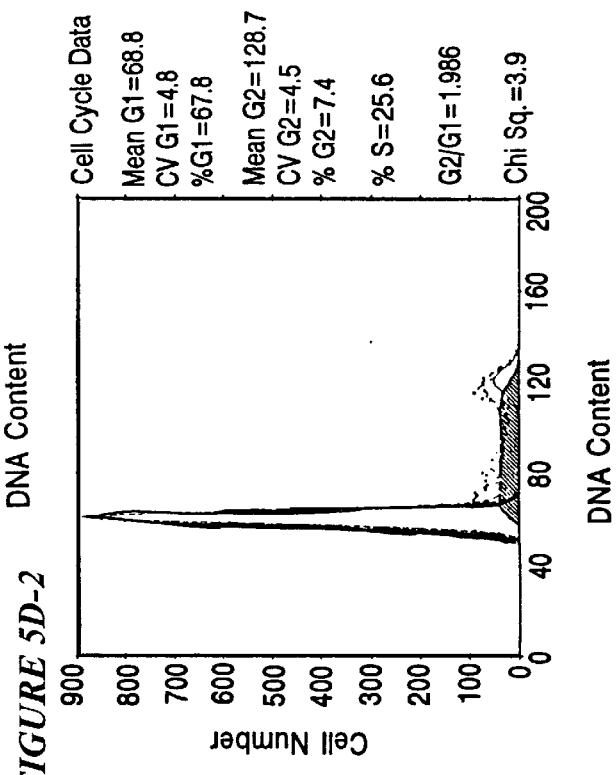
Figure 6A:
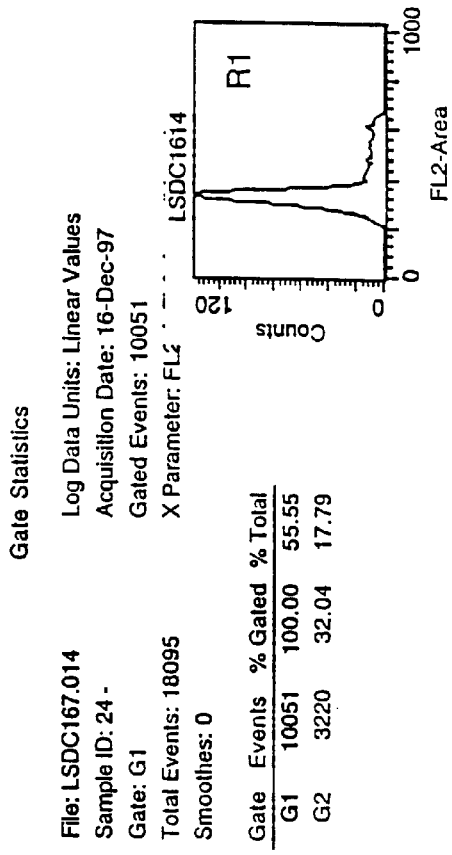
Figure 6B:
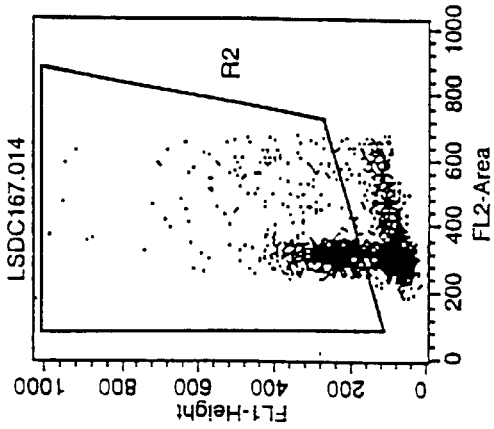
Figure 6C:
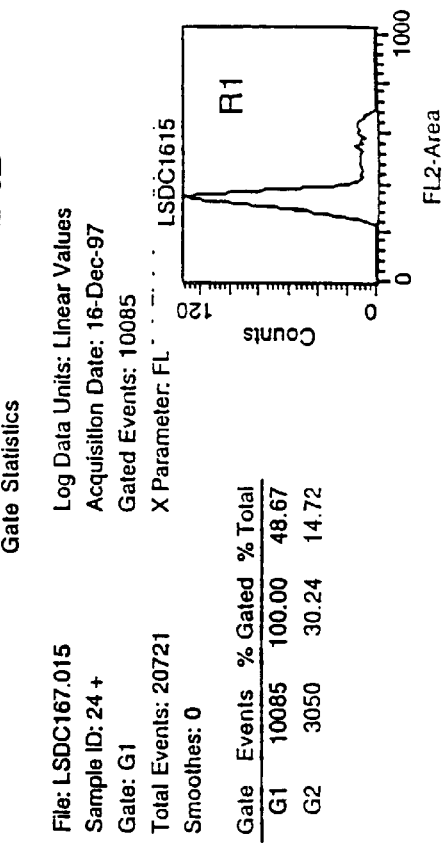
Figure 6D:
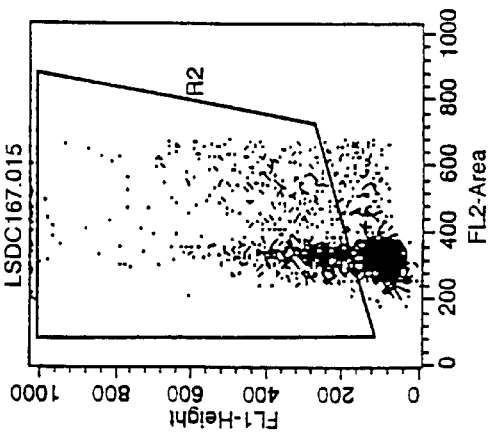
Figure 7A:
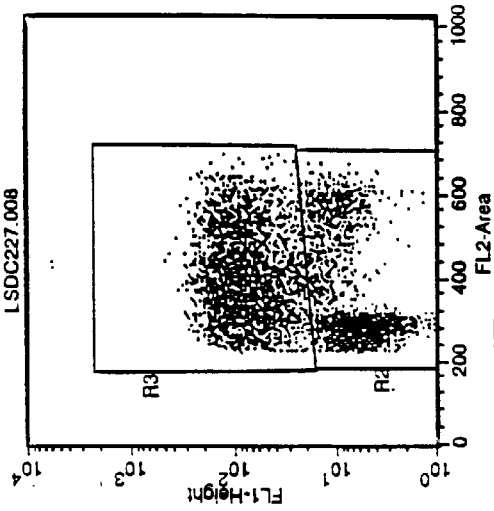
Figure 7B:
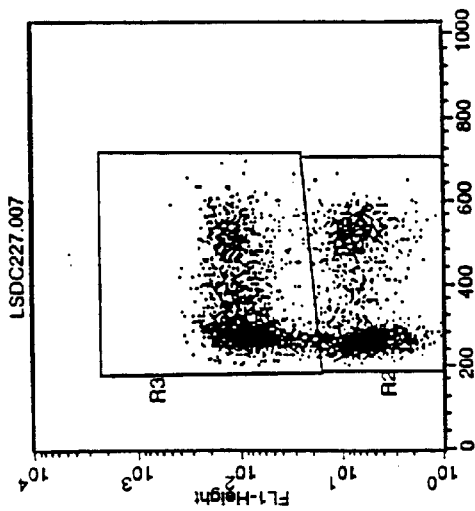
Figure 7C:
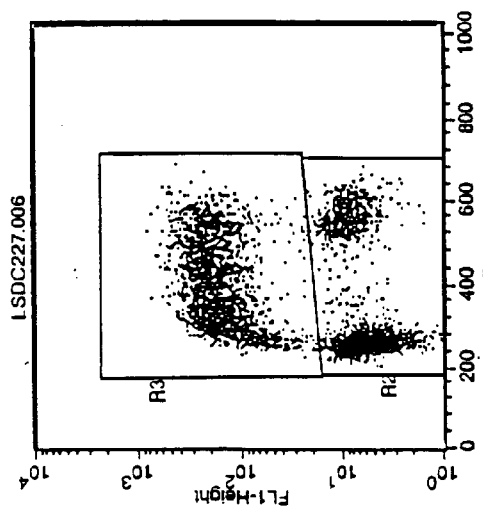
Figure 7D:
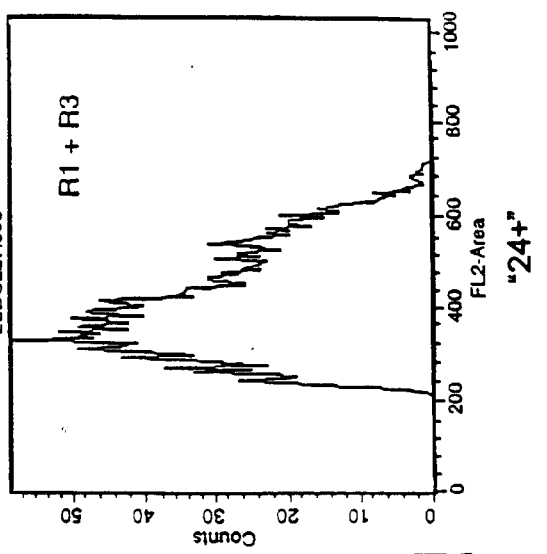
Figure 7E:
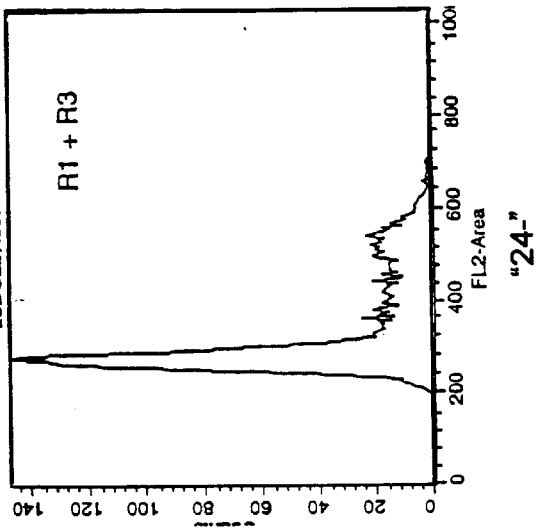
Figure 7F:
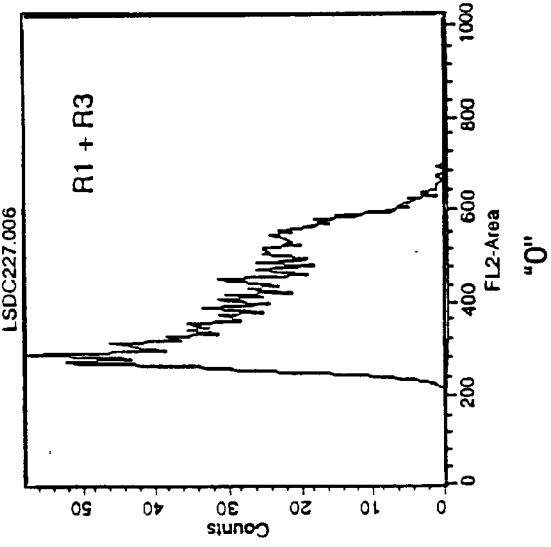

A 20 mM stock solution of dysidiolide was prepared in dimethylsulfoxide (DMSO) and a pilot experiment was carried out to measure the effects of the drug on the viability (Trypan blue exclusion) and flow cytometric parameters of four human cancer cell lines: the prostate lines TSU-Pr1, PC3 and DU145, and the breast line, MCF7. Cultures were treated with 0, 2, 10 and 50 μM dysidiolide for 24 hr. Dysidiolide was cytotoxic to the four lines as evidenced by the loss of Trypan blue exclusion capability and by the appearance of sub-G1 fraction on flow cytometric (FACS) analysis (FIGS. 3 and 4A–D). Histograms for DNA content demonstrated that dysidiolide induced changes in the cell cycle distribution on the four cell lines tested. The loss of a G2/M (4 n peak) was evident in PC3, DU145 and MCF7 cells at higher doses of drug (FIGS. 5B–D). (At 50 μM dysidiolide, the level of cell death was too high in TSU-Pr1 cells to fit a valid histogram (FIG. 5A)). These cell cycle changes are consistent with arrest prior to completion of the replicative (S) phase, or with cell death occurring preferentially in cells with a 4n DNA content (G2/M population).

To further analyze the cell cycle effects induced by dysidiolide, the effects of the drug on S phase progression were tested. For this purpose, a subset of cells was pulse-labeled with the thymidine analog, 5-bromodeoxyuridine (BrdU) for 30 min, and chased in the presence or absence of dysidiolide. The progression of this group of cells through the cell cycle was followed by flow cytometry, by analyzing the intensity of BrdU labeling and DNA content at two different wavelengths: red for propidium iodide stain (DNA content) and green for the detection of anti-BrdU antibodies coupled to fluorescein (Becton-Dickinson Immunocytometric Systems, San Jose, Calif.). The first experiment was conducted on MCF7 human breast cancer cells chased for varying time periods after a 30 min BrdU pulse, with or without 10 μM dysidiolide. After a 24 hr chase in the presence of the drug, fewer cells had reached G1 (FIG. 6). However, the effect was modest in intensity (approximately 45% less cells reached G1 in treated samples, compared with untreated controls)

Figure 8B:
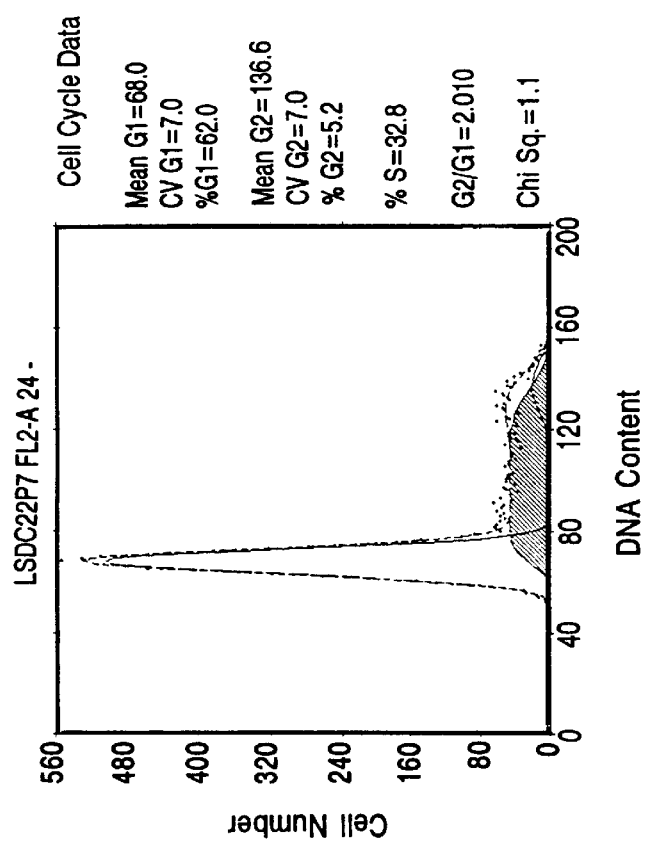
Figure 8A:
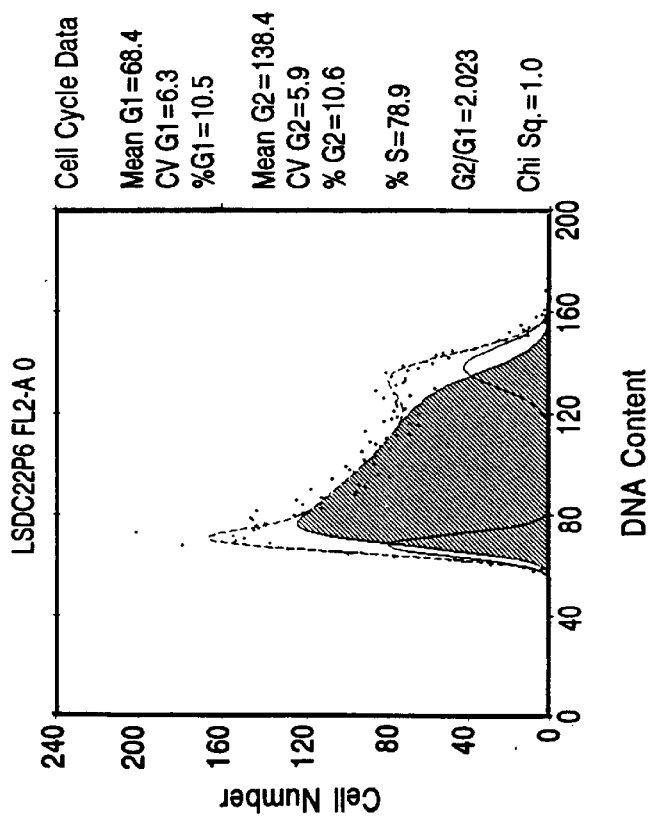

A second pulse-chase experiment was conducted on MCF7. Cells were labeled for 30 min with BrdU, and chased in the presence or absence of 50 μM dysidiolide for 24 hr. Samples were doubly stained (with propidium iodide (for DNA) and with anti-BrdU antibodies coupled to fluorescein) and subjected to FACS analysis. Samples were acquired and final analysis was received. As shown in FIG. 7, dysidiolide prevented cell cycle progression of BrdU-positive cells onto the next G1 phase of the cell cycle. The DNA content of the BrdU-positive cells in the drug-treated samples ("24+"), seems indistinguishable from the pattern obtained just after the BrdU pulse ("0"). On the other hand, BrdU-positive cells in DMSO-treated "control" cultures ("24–") were able to progress into G1 (2n DNA content) (compare FIGS. 5 A "0", B "24–" and C "24+"). One of the limitations of the cell cycle analysis program used in FACS analysis, is the inability of the program to fit a histogram when cells have an intermediate DAN content (2n<x<4n, "S phase"). A "forced" fit for the 24+ sample (dysidiolide treatment) showed that approximately 90% of the cells are in this stage see FIG. 8). Again, and as discussed above, accumulation of cells with an intermediate DNA content in response to dysidiolide could result from the induction of either S phase arrest, or DNA fragmentation and death of cells that have 4n DNA content (that will segregate to the left on a DNA content plot).

Figure 9A:
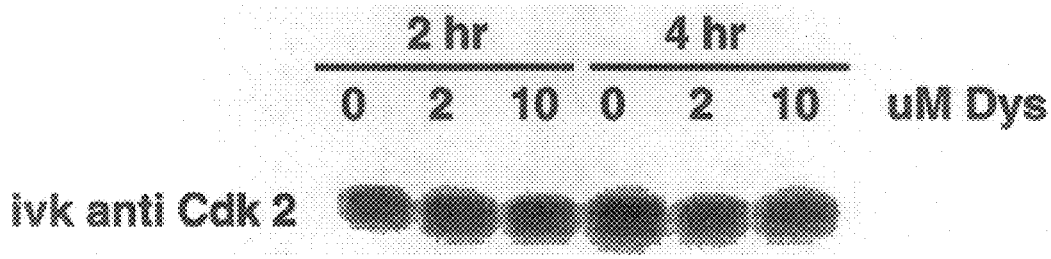
Figure 9B:
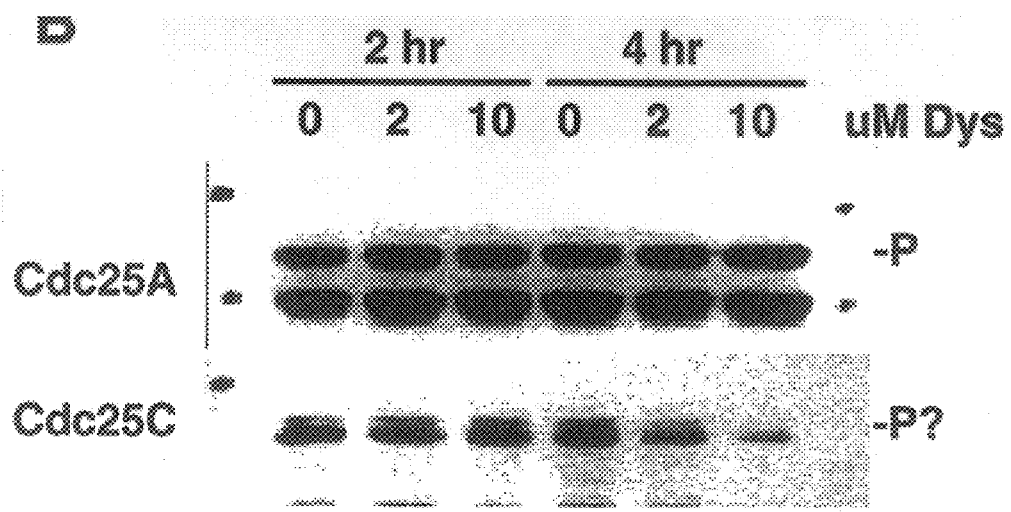

To further characterize the effects of dysidiolide on cell cycle control, experiments were conducted at the molecular level. As Cdc25s (A, B and C) are positive regulators of cyclin-dependent kinases (Cdk) (reviewed in Draetta and Eckstein, BBA 1332: M53–M63, 1997) inhibition of Cdc25 is expected to result in inhibition of Cdk activity. MCF7 cells were treated with 2 or 10 μM dysidiolide or with DMSO (controls) for 2 or 4 hr. Cell extracts were used to measure the steady-state levels of Cdc25 A and C, and Cdk activity. At this concentration and for these time periods, no significant changes were observed in Cdk2 activity (FIG. 9A). However, a decrease in the levels of Cdc25 C (but not on A) was clearly noticeable (FIG. 9B). In the next experiment MCF7 cells were treated for 24 hr with 50 μM dysidiolide or with DMSO (control) for 24 hr. As seen before, Cdc25 C, but not A, were reduced in drug-treated samples (FIG. 10). On the other hand, at these more stringent conditions, inhibition of Cdk2, Cdk4 and Cdc2 protein kinase activities was observed (FIG. 10A and FIG. 10B).

Treated cells also exhibited reduced levels of p21, p27, cyclin D1 and cyclin E (FIG. 10A)

RESULTS AND DISCUSSION

Synthesis of Dysidiolide

The power of the Gassman dioxolenium dienophile method is underscored by the fact that trisubstituted analogs of, bearing ester dienophiles instead of the acetal, were ineffective in the Diels Alder reaction. We also note that high selectivity for endo addition was observed when a dioxane acetal of Z-2-methyl-2-butenal was used as the dienophile in a Diels Alder reaction with diene (compound 14 of FIG. 1B). The adduct from this reaction was elaborated, leading to "dysidiolides" stereoisomeric with 1 at carbons 6 and 7.

In vivo and in Vitro Testing

Cdc25A is thought to regulate G1 progression, whereas Cdc25B and C regulate progression into mitosis, the fact that dysidiolide affects the activity of G1, S and G2/M cyclin-Cdks complexes might indicate that the drug is not specific for Cdc25A, but rather affects the three Cdc25s. It is also possible that some of the effects observed could be secondary to cell cycle arrest. These possibilities will be explored by carrying out the kinetic experiments discussed above.

In summary, the synthetic dysidiolide is an active drug in human tumor cell lines. It induces cytotoxicity, as detected by loss of Trypan blue exclusion and by the appearance of cells containing fragmented DNA via FACS analysis. Pulse-chase experiments in BdrU-labeled cells indicated that when cells replicating DNA receive dysidiolide, they are impaired in their ability to progress through the cell cycle. Furthermore, consistent with an inhibitory effect on the positive cell cycle regulator Cdc25, dysidiolide treatment induced the inhibition of Cdk activities (Cdk4, Cdk2 and Cdc2). Dysidiolide has the potential to be a cell cycle-targeted drug, which could be used alone or in combination with other treatments. In this regard, it may sensitize cells for DNA damaging treatments (i.e. act as a radiosensitizer). Dysidiolide inhibited the growth of a number of human tumor cancer lines with IC50 ranging from 0.5 to 4.5 μM. The antitumor effect was independent of expression of the MDR phenotype, as there was no cross-resistance with vinblastine or doxorubicin (cf.MCF7 vs. MCF/Adr and CEM vs. CEM/VBL100, Table I). Cell lines derived from tumors of diverse origins were affected similarly.

REFERENCES

1. Gunasekera, S. P.; McCarthy, P. J.; Kelly-Borges, M.; Lobkovsky, E.; Clardy, J. *J. Am. Chem. Soc.* 1996, 118, 8759.
2. Millar, J. B. A.; Russell, P. *Cell* 1992, 68, 407.
3. Baratte, B.; Meijer, L.; Galaktionov, K.; Beach, D. *Anticancer Res.* 1992, 12, 873.
4. For examples of Diels Alder reactions using allylic acetals as the dienophile see: a) Gassman, P. G.; Singleton, D. A.; Wilwerding, J. J.; Chavan, S. P. *J. Am. Chem. Soc.* 1987, 109, 2182. b) Sammakia, T.; Berliner, M. A. *J. Org. Chem.* 1994, 59, 6890.
5. For examples of Diels Alder reactions using vinyl oxolenium ions derived from different dienophiles see: a) Gassman, P. G.; Chavan, S. P. *J. Org. Chem.* 1988, 53, 2392. b) Gassman, P. G.; Chavan, S. P. *Tetrahedron Lett.* 1988, 29, 3407. c) Gassman, P. G.; Chavan, S. P. *J. Chem. Soc., Chem. Commun.* 1989, 837. d) Hashimoto, Y.; Saigo, K.; Machida, S.; Hasegawa, M. *Tetrahedron Lett.* 1990, 39, 5625. e) Hashimoto, Y.; Nagashima, T.; Hasegawa, M.; Saigo, K. *Chem. Lett.* 1992, 1353. f) Sipf. P.; Xu, W. *Tetrahedron* 1995, 51, 4551.
6. For an example of a Diels Alder reaction with a similar diene giving exo-selectivity see: Yoon, T.; Danishefsky, S. J.; de gala, S. *Angew, Chem. Int. Ed. Engl.* 1994, 33, 85.
7. a) Giusti, G. *Bull. Chim. Soc. Fr.* 1972, 753. b) Le Coq, A.; Gorgues, A. *Org. Synth.* 1988, Coll. Vol. 6, 954.
8. Alexakis, A.; Commercon, A.; Coulentianos, C.; Normant, J. F. *Tetrahedron*, 1984, 40, 715.
9. a) Ansell, M. F.; Thomas, D. A. *J. Chem. Soc.* 1961, 539. b) Mazzocchi, P. H.; Wilson, P.; Khachik, F.; Klinger, L.; Minamikawa, S. *J. Org. Chem.* 1983, 48, 2981.
10. Krafft, M. E.; Holton, R. A. *Tetrahedron Lett.* 1983, 24, 1345.
11. Spijker-Assink, M. B.; Robijn, G. W.; Ippel, J. H.; Lutenburg, J. *Recl. Trav. Chim. Pay-Bas* 1992, 111, 29.
12. Stang, P. J.; Treptow, W. *Synthesis* 1980, 283.
13. Scott, W. J.; Stille, J. K. *J. Am. Chem. Soc.* 1986, 108, 3033.
14. The desired relative stereochemistry of adduct 15 was confirmed by X-ray crystal analysis of the lactol produced by removal of the silyl and acetal protecting groups.
15. Gautier, E. C. L.; Graham, A. E.; Makillop, A.; Standen, S. P.; Taylor, R. J. K. *Tetrahedron Lett.* 1997, 38, 1881.
16. Hagiwara, H.; Inome, K.; Uda, K. *J. Chem. Soc., Perkin Trans.* I 1995, 757.
17. The undesired C4 epimer of 19 may be recycled, via oxidation to the ketone and subsequent reduction, to the desired stereoisomer. The reduction gives a mixture of C4 diastereomers that is processed. Alternatively, the undesired C4 epimer of 19 may be converted into the desired compound (81%) yield) using a Mitsunobu inversion with p-nitrobenzoic acid and reduction of the resulting ester. See: Martin, S. F.; Dodge, J. A. *Tetrahedron Lett.* 1991, 32, 3017.
18. Kernan, M. R.; Faulkner, D. J. *J. Org. Chem.* 1988, 53, 2773.

What is claimed is:
1. A process for the preparation of a racemic mixture of dysidiolide analogue of the formula:

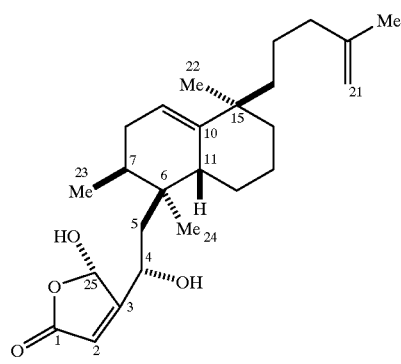

comprising the steps of:

(a) adding lithium dimethylcuprate to a dioxolane;
(b) trapping the compound formed in step (a) under suitable conditions to form an olefin;
(c) converting the ester function to a protected two carbon alcohol residue to form a dienophile;
(d) converting a ketone, derived by alkylating with an alkyl iodide, to vinyl triflate;
(e) performing a Stille cross coupling on the vinyl triflate of (d) under suitable conditions to form a diene;
(f) performing a Diels Alder reaction on the dienophile of step (c) and the diene of step (e) under suitable conditions to form a compound having the structure:

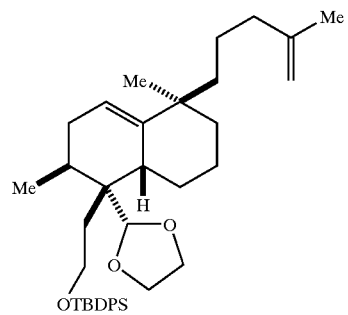

(g) cleaving the acetal function of the compound in (f) under suitable conditions to form a compound having the structure:

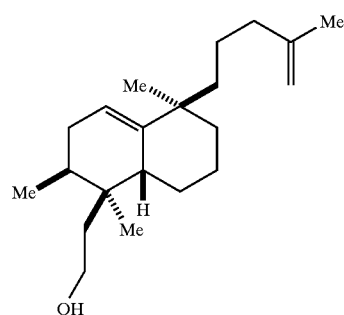

(h) performing a Wolff Kishner reduction and desilylating the compound in step (g) to form an alcohol having the structure:

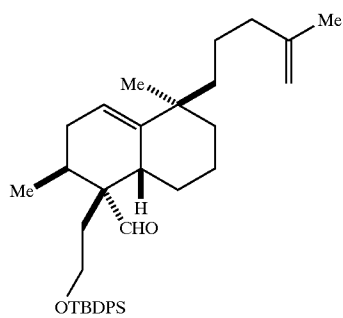

(i) oxidizing the alcohol formed in step (h) under suitable conditions to form an aldehyde;

(j) treating the aldehyde in step (i) with 3-lithiofuran and photo-oxidizing under suitable conditions to form a racemic mixture of dysidiolide.

2. A product produced by the process of claim 1.

3. A pharmaceutical composition comprising the compound of claim 1.

4. A compound having the structure:

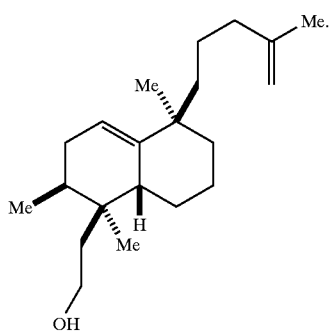

5. A compound having the structure:

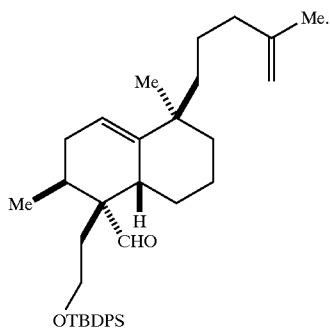

6. A compound having the structure:

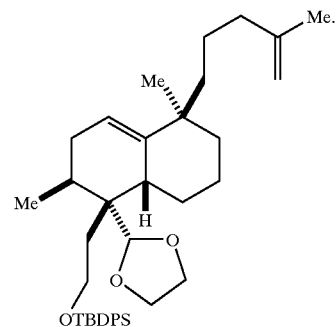

7. A method for inhibiting growth of cancerous cells comprising contacting an amount of a racemic mixture of dysidiolide effective to inhibit the growth of said cells.

8. The method of claim 7, wherein the amount comprises a quantity of the compound to inhibit, reduce, or cause remission of the cells.

9. A method for treating cancer in a subject which comprises administering to the subject a therapeutically effective amount of racemic mixture of dysidiolide.

10. The method of claim 9, wherein the cancer is of the breast, colon, lung, liver, brain or ovary.

11. The method of claim 10, wherein the therapeutically effective amount comprises an amount of the compound to inhibit, reduce, or cause remission of the cancer.

12. The method of claim 11, wherein the therapeutically effective amount is an amount from about to 50 to about 5000 mm$^3$/day.

13. The method of claim 11, wherein the therapeutically effective amount is an amount from about to 50 to about 500 mm$^3$/day.

14. The method of claim 11, wherein the therapeutically effective amount is an amount from about to 60 to about 275 mm$^3$/day.

15. The method of claim 11, wherein the therapeutically effective amount is an amount from about 0.5 to 50 mg/kg body weight.

16. The method of claim 11, wherein the therapeutically effective amount is an amount from about 5 to 10 mg/kg body weight.

17. The method of claim 11, wherein the administration comprises epidural, intraperitoneal, intramuscular, subcutaneous or intravenous injection; infusion; or topical, nasal, oral, anal, ocular or otic delivery.

* * * * *